US007015205B1

(12) United States Patent
Wallack et al.

(10) Patent No.: US 7,015,205 B1
(45) Date of Patent: Mar. 21, 2006

(54) MELANOMA VACCINE AND METHODS OF MAKING AND USING SAME

(75) Inventors: Marc K. Wallack, New York, NY (US); Muthukumaran Sivanandham, S. Ozone Park, NY (US)

(73) Assignee: St. Vincent's Hospital and Medical Center of New York, New York, NY (US)

( * ) Notice: Subject to any disclaimer, the term of this patent is extended or adjusted under 35 U.S.C. 154(b) by 0 days.

(21) Appl. No.: 09/691,504

(22) Filed: Oct. 18, 2000

Related U.S. Application Data

(60) Provisional application No. 60/240,933, filed on Oct. 18, 1999, now abandoned.

(51) Int. Cl.
| | |
|---|---|
| A61K 48/00 | (2006.01) |
| C12N 5/00 | (2006.01) |
| C12N 15/63 | (2006.01) |
| C12N 15/87 | (2006.01) |

(52) U.S. Cl. ............... 514/44; 424/93.2; 424/93.1; 435/320.1; 435/325; 435/455

(58) Field of Classification Search ............ 435/320.1, 435/325, 455; 424/93.1, 93.2; 514/44
See application file for complete search history.

(56) References Cited

U.S. PATENT DOCUMENTS

| | | | | |
|---|---|---|---|---|
| 4,108,983 | A | 8/1978 | Wallack | 424/89 |
| 4,863,727 | A | 9/1989 | Zimmerman et al. | 424/85.2 |
| 5,030,621 | A | 7/1991 | Bystryn | 514/21 |
| 5,066,489 | A | 11/1991 | Paradise et al. | 424/85.2 |
| 5,290,551 | A | 3/1994 | Berd | 424/88 |
| 5,425,940 | A | 6/1995 | Zimmerman et al. | 424/85.1 |
| 5,478,556 | A | 12/1995 | Elliott et al. | 424/852 |
| 5,484,596 | A | 1/1996 | Hanna, Jr. et al. | 424/277.1 |
| 5,635,188 | A | 6/1997 | Bystryn | 424/277.1 |
| 5,788,963 | A | 8/1998 | Murphy et al. | 424/93.21 |

OTHER PUBLICATIONS

Sivanandham et al. (1994) J. Immunol. Immunother., vol. 38, 259-264.*
Nestle et al. (1998) Nat. Med., vol. 4, No. 3, 328-332.*
Pardoll (1998) Nat. Med. vol. 4 (5 Suppl), 525-531.*
Kaufman (1995) Annu. Rev. Immunol., vol. 13.*
Tueting T. et al., "Autologous Human Monocyte-derived Dendritic Cell Genetically Modified to Express Melanoma Antigens Elicit Primary Cytotoxic T Cell Responses in Vitro: Enhancement by Cotransfection of Genes Encoding the Th1-biasing Cytokines IL-12 and IFN-$\alpha^{1}$", J. Immunol. vol. 160, 1998, pp. 1139-1147.
Quin H. et al., "Recombinant Vaccinia Expressing Interleukin-2 for Cancer Gene Therapy", Cancer Gene Therapy, vol. 3, No. 3, 1996, pp. 163-167.
Abde-Wahab Z. et al., "Human Dendritic Cells, Pulsed with Either Melanoma Tumor Cell Lysates or the Gp100 Peptide (280-288), Induce Pairs of T-cell Cultures with Similar Phenotype and Lytic Activity", Cellular Immunology, vol. 186, No. 1, May 25, 1998 (pp. 63-74).
Sivanandham M. et al., "Prospects for Gene Therapy and Lymphokine Therapy for Metastatic Malanoma", Ann. Plastic Surg., vol. 28, No. 1, 1992, pp. 114-118.
Mukherji B and Chakraborty NG., "Immunobiology and immunotherapy of melanoma," Curr.Opin.Oncol.7:175-184, 1995.
Wallack MK, Sivanandham M, Balch CM, et al., "Favorable Clinical Responses In Subsets of Patients From A Randomized, Multi-Institutional Melanoma Vaccine Trial," Ann. Surg.Oncol.3(2):1-8, 1996.
Lotze MT et al., "High dose recombinant interleukin-2 in the treatment of patients with disseminated cancers," JAMA 256(22):3117-3124, 1986.
West WH et al., "Constant infusion of recombinant IL-2 in adoptive immunotherapy of advanced cancers," New Engl. J.Med. 316(15):898-905, 1987.
Qin H, Catterjee SK, "Cancer gene therapy using tumor cells infected with recombinant vaccinia virus expressing GM-CSF," Hum. Gene Ther. 7(15):1853-60, Oct. 1, 1996.
Shrayer DP, Bogaars H, Hearing VJ, Wanebo HJ, "Immunization of mice with irradiated melanoma tumor cells transfected to secrete lymphokines and coupled with IL-2 or GM-CSF therapy," J.Exp.Ther.Oncol., 1(2):126-33, 1996.
Rosenberg et al., "Use of tumor-infiltrating lymphocytes and interleukin-2 in the immunotherapy of patients with metastatic melanoma," New Engl.J.Med.319:1676-1680, 1988.
Dutcher et al., "A Phase II study of high-dose continuous infusion interleukin-2 with lymphokine-activated killer cells in patients with metastatic melanoma," J.Clin.Oncol. 9(4): 641-648, 1991.
Siegel et al., "Interleukin-2 toxicity," J.Clin.Oncology, 9: 694-704, 1991.
Pardoll DM,"Cancer vaccines," Nat.Med. 4(5 Suppl): 525-31, 1998.

(Continued)

Primary Examiner—Anne M. Wehbe'
(74) Attorney, Agent, or Firm—Kenyon & Kenyon

(57) ABSTRACT

An immunotherapeutic vaccine providing antigen presenting cells that have been pulsed with a disrupted cell preparation which includes enucleated cytosol and cell membranes of cancer cells infected with a recombinant vaccinia virus encoding at least one immunostimulating molecule. In a preferred embodiment, the vaccine includes autologous dendritic/monocytic cells (DC/M) that present a mixture of antigens (present in the enucleated cytosol and cell membranes) from melanoma cell lines that have been infected with a recombinant vaccinia virus encoding IL-2. In another of the preferred embodiments, the enucleated cytosol and cell membranes are from melanoma cells harvested from the patient to be treated. A method of making the vaccine and methods of using the vaccine to stimulate an anti-cancer immune response and to treat a patient with a cancer are also described.

38 Claims, 7 Drawing Sheets

OTHER PUBLICATIONS

Nestle FO et al., "Vaccination of melanoma patients with peptide- or tumor lysate pulsed dendritic cells," Nat.Med.4 (3):328-332, 1998.

Hsu et al., "Vaccination of patients with B-cell lymphoma using autologous antigen-pulsed dendritic cells," Nat.Med. 2(1):52-58, 1996.

Villikka K et al, "Cytokine therapy of maglignant melanoma," Ann.Med.28(3):227-233, 1996.

Kirkin AF et al., "Generation of human-melanoma-specific T lymphocyte, clones defining novel cytolytic targets with panels of newly established melanoma cell lines," Cancer Immunol. Immunother.41(2):71-81, 1995.

Celluzzi CM et al., "Cutting Edge: Physical interaction bewteen dendritic cells and tumor cells results in an immunogen that induces protective and therapeutic tumor rejection," J.Immunol.160(7):3081-3085, 1998.

Flexner C et al., "Prevention of vaccinia virus infection in immunodeficient mice by vector-directed IL-2 expression," Nature 330:259-262, 1987.

Sivanandham M et al., "Therapeutic effect of a vaccinia colon oncolysate prepared with interleukin-2-gene encoded vaccinia virus studied in a syngeneic CC-36 murine colon hepatic metastasis model," Cancer Immunol. Immunother. 38:259-264, 1994.

Lee SS et al., Vaccinia virus vector mediated cytokine gene transfer for in vivo tumor immunotherapy, Proc.Am.Assoc. Can.Res.1035:514, 1994.

Miyahira Y et al., "Quantification of antigen specific CD8+ T cells using an ELISPOT assay", J. Immunol.Meth.181: 45-54, 1995.

* cited by examiner

MELANOMA VACCINE AND METHODS OF MAKING AND USING SAME

CROSS REFERENCE TO RELATED APPLICATION

This application claims priority to patent application Ser. No. 60/240,933 filed Oct. 18, 1999 now abandoned, which is incorporated herein by reference in its entirety.

FIELD OF THE INVENTION

The invention generally relates to an improved therapeutic vaccine useful for treatment and prevention of a cancer. Disclosed are a cancer vaccine, and methods of making and using such a vaccine in a host diagnosed with a cancer. The vaccine as used in accordance with the present invention comprises a new administration schedule and ingredients such as recombinant IL-2 encoding vaccinia virus and autologous dendritic/monocytic cells pulsed with melanoma antigens derived from cancerous melanoma cell lines expressing at least two HLA class I A antigens.

BACKGROUND OF THE INVENTION

The incidence of malignant melanoma has increased at an alarming rate over the past few decades, and indications are that the incidence of this deadly disease will continue to rise in the future. As melanoma is known to be refractory to conventional chemotherapy or radiotherapy, several alternative treatment approaches have been used for treatment of this variety of skin cancer. Immunotherapy has been considered potentially useful for melanoma because melanoma has shown certain immunological traits, such as spontaneous regression, infiltration of lymphocytes within the tumor mass, an in vitro demonstration of anti-melanoma specific cellular responses, and evidence of responsiveness to immunomodulators such as interleukins and interferons. (Mukherji B and Chakraborty N G., Immunobiology and immunotherapy of melanoma, Curr. Opin. Oncol. 7:175–184, 1995). For example, immunizing a patient having a melanoma with its own melanoma antigens prepared as a vaccine might induce an anti-tumor immune reaction and thus could cure such a patient from the disease.

The description of one such vaccine can be found in U.S. Pat. No. 4,108,983 to Wallack. This patent describes a first generation melanoma vaccine, Vaccinia Melanoma Oncolysate (VMO), which was derived from melanoma cells lysed by a vaccinia virus (U.S. Pat. No. 4,108,983). This vaccine and modified versions thereof were tested in multiple clinical trials. Although a clinical benefit was seen in several subsets of patients, especially in young male patients with stage III (AJCC) melanoma, the vaccine did not produce a significant benefit for melanoma patients when tested as a surgical adjuvant therapy in a recently completed phase III clinical trial. (Wallack M K, Sivanandham M, et al., Favorable clinical responses in subsets of patients from a randomized, multiinstitutional melanoma vaccine trial, Ann. Surg. Oncol. 3(2):1–8, 1996; Wallack M K, Sivanandham M, Balch C M, et al., A phase III randomized, double-blind, multiinstitutional trial of vaccinia melanoma oncolysate-active specific immunotherapy for patients with stage II melanoma, Cancer 75:34–42, 1995).

U.S. Pat. Nos. 5,635,188 and 5,030,621 both to Bystryn, disclose a vaccine made up of cell surface antigens of melanoma cells that are shed into the culture medium and consequently used as anti-melanoma vaccine.

Similarly, U.S. Pat. No. 5,484,596 to Hanna, Jr. et al. discloses a method of cancer therapy consisting of preparing irradiated tumor cells and injecting them as a vaccine into a human patient.

Although such immunotherapy trials with these vaccines have shown encouraging results in some patients, e.g., partial regression of melanoma, delay in the appearance of recurrent melanoma, and an increase in overall survival as compared to standard therapy or surgery, none of the methods so far have been entirely satisfactory.

During the last two decades, several new immunomodulating cytokines were discovered, and these cytokines have been extensively studied for their therapeutic benefit in patients with cancer. The most studied cytokine is interleukin-2 (IL-2), which has shown some benefit in augmenting immunity against melanoma. The benefit of IL-2 therapy is presumed to be due to the stimulation of T cells, some of which may have become toxic toward tumor cells.

Generally, immunomodulating cytokines such as IL-2 are administered either as a bolus injection or as a low dose continuous infusion (Lotze M T et al., High dose recombinant interleukin-2 in the treatment of patients with disseminated cancers, JAMA 256(22):3117–3124, 1986; West W H et al., Constant infusion of recombinant IL-2 in adoptive immunotherapy of advanced cancers, New Engl. J. Med. 316(15):898–905, 1987). However, bolus injection with a high dose of cytokines generally produces significant toxicity while low dose continuous infusion is inconvenient. A more constant level of cytokine in vivo, similar to that produced by continuous infusion of cytokine, can be achieved using recombinant viruses or bacteria designed to produce cytokines in vivo.

The use of recombinant vectors to induce the production of cytokines in vivo falls within the definition of gene therapy. Some encouraging results have been seen using such vectors. For example, use of the IL-2 gene in recombinant vaccinia virus (rVV) seemed to reduce tumor burden in a mouse melanoma model (Sivanandham M, Scoggin S D, Sperry R G, Wallack M K, Prospects for gene therapy and lymphokine therapy for metastatic melanoma, Ann. Plast. Surg. 28(1):114–118, 1992). In contrast, later studies indicated that recombinant vaccinia with IL-2 had no effect. For example, Qin et al. describe a vaccine that appeared to have some effect with rVV expressing GM-CSF, but not with rVV expressing IL-2. (Qin H, Chatterjee S K, Cancer gene therapy using tumor cells infected with recombinant vaccinia virus expressing GM-CSF, Hum. Gene Ther. 7(15): 1853–60, 1996). Similar disappointing results with rVV encoding IL-2 were observed by Shrayer et al. in their melanoma model. (Shrayer D P, Bogaars H, Hearing V J, Wanebo H J, Immunization of mice with irradiated melanoma tumor cells transfected to secrete lymphokines and coupled with IL-2 or GM-CSF therapy, J. Exp. Ther. Oncol., 1(2):126–33, 1996).

Thus, the success of recombinant IL-2 in gene therapy strategies is unpredictable. Initial reports showed objective response rates with single-agent rIL-2 therapy in the range of 15% to 20%; however, the overall response rates in clinics were much lower than originally anticipated. In addition, it appears that co-administration of lymphokine-activated killer (LAK) cells, generated ex vivo with rIL-2, does not enhance the response rates achieved with rIL-2 alone.

For example, U.S. Pat. Nos. 4,863,727 and 5,425,940, both to Zimmerman et al., disclose augmentation of anti-melanoma activity in mammals by administering an effective amount of IL-2 and tumor necrosis factor (TNF), or TNF and interferon (IFN)-beta, or IL-2, TNF, and IFN-beta combinations. These compositions were also suggested to be useful for treating other cancers such as leukemia, lymphoma, mastocytoma, mammary adenocarcinoma, and pharyngeal squamous cell carcinoma.

U.S. Pat. No. 5,066,489 to Paradise et al., discloses treatment of malignant melanoma by combining IL-2 with chemotherapeutic agents.

Rosenberg et al. describe a combination of IL-2 with tumor-infiltrating lymphocytes as a means of providing an immunotherapy to patients with metastatic melanoma (Rosenberg et al., Use of tumor-infiltrating lymphocytes and interleukin-2 in the immunotherapy of patients with metastatic melanoma, New Engl. J. Med. 319:1676–1680, 1988).

Similarly, Dutcher et al. described combining IL-2 with IL-2-activated killer cells as a treatment option for metastatic melanoma. (Dutcher et al., A Phase II study of high-dose continuous infusion interleukin-2 with lymphokine-activated killer cells in patients with metastatic melanoma, J. Clin. Oncol. 9(4):641–648, 1991).

Because of the broad activation nature of T cells, the anti-tumor response generated by IL-2 is not very specific. For that reason, IL-2-based therapy has not proven to be very effective. In addition, the doses of IL-2 required by these IL-2 treatment methods appear toxic to treated patients. (Siegel et al., Interleukin-2 toxicity, J. Clin. Oncology, 9:694–704, 1991). Based on these observations, it was believed that a more specific immune response can be generated by combining IL-2 with tumor specific antigens.

U.S. Pat. No. 5,290,551 to Berd, discloses the treatment of melanoma with a vaccine comprising irradiated autologous melanoma tumor cells conjugated to a hapten and combining the vaccine with IL-2.

U.S. Pat. No. 5,478,556 to Elliott et al., discloses vaccination of cancer patients using tumor-associated antigens mixed with IL-2 and granulocyte-macrophage colony stimulating factor (GM-CSF).

The importance of antigen presenting (APC) or accessory cells in inducing specific cellular immune response was postulated long ago. Among many types of accessory cells are dendritic cells (DC), which are derived from various cell lineages such as bone marrow stem cells, macrophages and lymphocytes. The DC stimulate cytotoxic and helper T-cells by expressing high levels of HLA class I and class II antigens and the T-cell co-stimulatory factors CD80, CD86, ICAM-1 and LFA-3. DC also secrete cytokines such as IL-12, IL-15 and IFN-gamma, which have been shown to be useful for the expansion of stimulated T-cells. DC-based immunotherapies have also been studied in patients with cancers and viral diseases.

To elicit anti-tumor immune response, various cell types have been employed as cellular adjuvants with tumor antigens, and recently several groups have shown that dendritic cells (DC), cultured with tumor cell lysates, synthetic tumor antigens, or peptides purified from tumor cells, induced rather significant anti-tumor immunity in vivo. In all of these approaches, the DC were pulsed with an exogenous source of antigen. Alternative methods were also proposed consisting of genetically engineering DC to express tumor antigens. The expression of tumor antigens by DC is a potent method of inducing tumor antigen-specific responses in vivo. (See Pardoll D M, Cancer vaccines. Nat. Med. 4(5 Suppl): 525–31, 1998). Several melanoma-specific antigens were identified recently, e.g., MART-1/Melan A, gp100, tyrosinase, MAGE-1, MAGE-3, and others. They were accordingly used to elicit anti-tumor immune reaction through presentation via DC. Some studies used not only peptides but unfractionated tumor cell lysates as well (Abdel-Wahab Z, DeMatos P, Hester D, Dong X D, and Seigler H F, Human dendritic cells, pulsed with either melanoma tumor cell lysates or the gp100 peptide (280–288), induce pairs of T-cell cultures with similar phenotype and lytic activity, Cell. Immunol. 186(1):63–74, 1998).

Thus, despite the fact that vaccination with autologous DCs was determined to be safe, the efficacy of such vaccines was not any better than with conventional melanoma vaccines. For example, the objective responses were evident only in 5 out of 16 patients with metastatic melanoma. (Nestle F O, Alijagic S, Gilliet M, Sun Y, Grabbe S, Dummer R, Burg G, Schadendorf D, Vaccination of melanoma patients with peptide- or tumor lysate pulsed dendritic cells, Nat. Med. 4(3):328–332, 1998). This and other similar approaches have failed to improve DC-based vaccines and to enhance the chances of survival of melanoma patients. Despite many studies relating to melanoma vaccine development, so far little real progress has been achieved. Clearly, there is a need for an effective melanoma vaccine useful to slow the progression of, if not cure, melanoma in a higher proportion of patients than in any earlier described vaccines.

U.S. Pat. No. 5,788,963 to Murphy et al., discloses methods and compositions for using human DC to activate T cells for immunotherapeutic responses against primary and metastatic prostate cancer. Other DC based approaches have also been described, e.g. Hsu et al. (Vaccination of patients with B-cell lymphoma using autologous antigen-pulsed dendritic cells, Nat. Med. 2(1):52–58, 1996).

Thus, while multiple approaches to melanoma (and cancer generally) have been undertaken during the last twenty years, and some progress made, the problem has remained. Melanoma continues to be on the rise and refractory to available therapies. (Villikka K, Pyrhonen S. Cytokine therapy of malignant melanoma. Ann. Med. 28(3):227–233, 1996).

Thus, the present invention provides an improved melanoma vaccine that provides a better success rate than the melanoma therapies existing in the prior art.

SUMMARY OF THE INVENTION

The present invention provides a therapeutic composition made up of antigen presenting cells that have been pulsed with a disrupted cell preparation. The disrupted cell preparation includes enucleated cytosol and cell membranes of cancer cells that have been infected with a recombinant vaccinia virus that encodes for at least one immunostimulating molecule. In one embodiment, the invention provides a therapeutic vaccine in which autologous dendritic/monocytic cells (DC/M) present a mixture of antigens (present in a preparation of enucleated cytosol and cell membranes) that are from cells from cancer cell lines that have been infected with a recombinant vaccinia virus encoding IL-2. In another embodiment, the enucleated cytosol and cell membranes are from cancer cells harvested from a patient's own cancer. In yet another embodiment, the antigen presenting cells are HLA-matched dendritic/monocytic cells for the host receiving the vaccine. According to the present invention the enucleated cytosol is substantially free of cell nuclei. In addition, the cancer cell membranes of the invention contain at least two and preferably more than two HLA class I A antigens.

The present invention also provides an immunotherapeutic vaccine having two parts. The first part of the vaccine involves administering a recombinant vaccinia virus encoding at least one immunostimulating molecule. The second part of the vaccine provides antigen presenting cells that have been pulsed with a preparation of antigens from cancer cells infected with a recombinant vaccinia virus encoding at least one immunostimulating molecule. In a preferred embodiment, the recombinant vaccinia virus of the first part of the vaccine encodes IL-2 and the second part of the vaccine comprises autologous DC/M that have been pulsed with enucleated cytosol and cell membranes from cancer cells of cancer cell lines which have been infected with recombinant vaccinia virus encoding IL-2.

The invention further provides a method of preparing an immunotherapeutic vaccine useful for creating an anti-cancer immune response or treating a host for cancer. This method includes the following steps: (i) contacting cancer cells with a recombinant vaccinia virus encoding an immunostimulating molecule; (ii) disrupting the vaccinia virus-contacted cancer cells to obtain a preparation of enucleated cytosol and cell membranes from the vaccinia-infected cancer cells; and (iii) pulsing antigen presenting cells with the preparation for a time sufficient for the antigens in the preparation to be presented on the surface of the APC.

Also included in the invention is a method for eliciting an anti-cancer immune response in a subject by administering a therapeutically effective amount of a composition including antigen presenting cells that have been pulsed with a preparation including enucleated cytosol and cell membranes of cancer cells infected with a recombinant vaccinia virus encoding for at least one immunostimulating molecule.

In addition, the invention provides for a method of eliciting an anti-cancer immune response in a subject by: (i) administering a recombinant vaccinia virus encoding at least one immunostimulating molecule; and (ii) administering a composition providing antigen presenting cells pulsed with a preparation including enucleated cytosol and cell membranes of cancer cells infected with a recombinant vaccinia virus encoding for at least one immunostimulating molecule. In yet another preferred embodiment, the first part of the vaccine is administered approximately thirty (30) minutes prior to the second part and in substantially the same location on the patient.

The present invention also provides a method of treating a subject for cancer by: (i) administering a recombinant vaccinia virus encoding at least one immunostimulating molecule; and (ii) administering a composition comprising antigen presenting cells pulsed with a preparation including enucleated cytosol and cell membranes of cancer cells infected with a recombinant vaccinia virus encoding at least one immunostimulating molecule. In yet another preferred embodiment, the first part of the vaccine is administered approximately thirty (30) minutes prior to the second part and in substantially the same location on the patient.

DETAILED DESCRIPTION OF THE INVENTION

Figure 1:
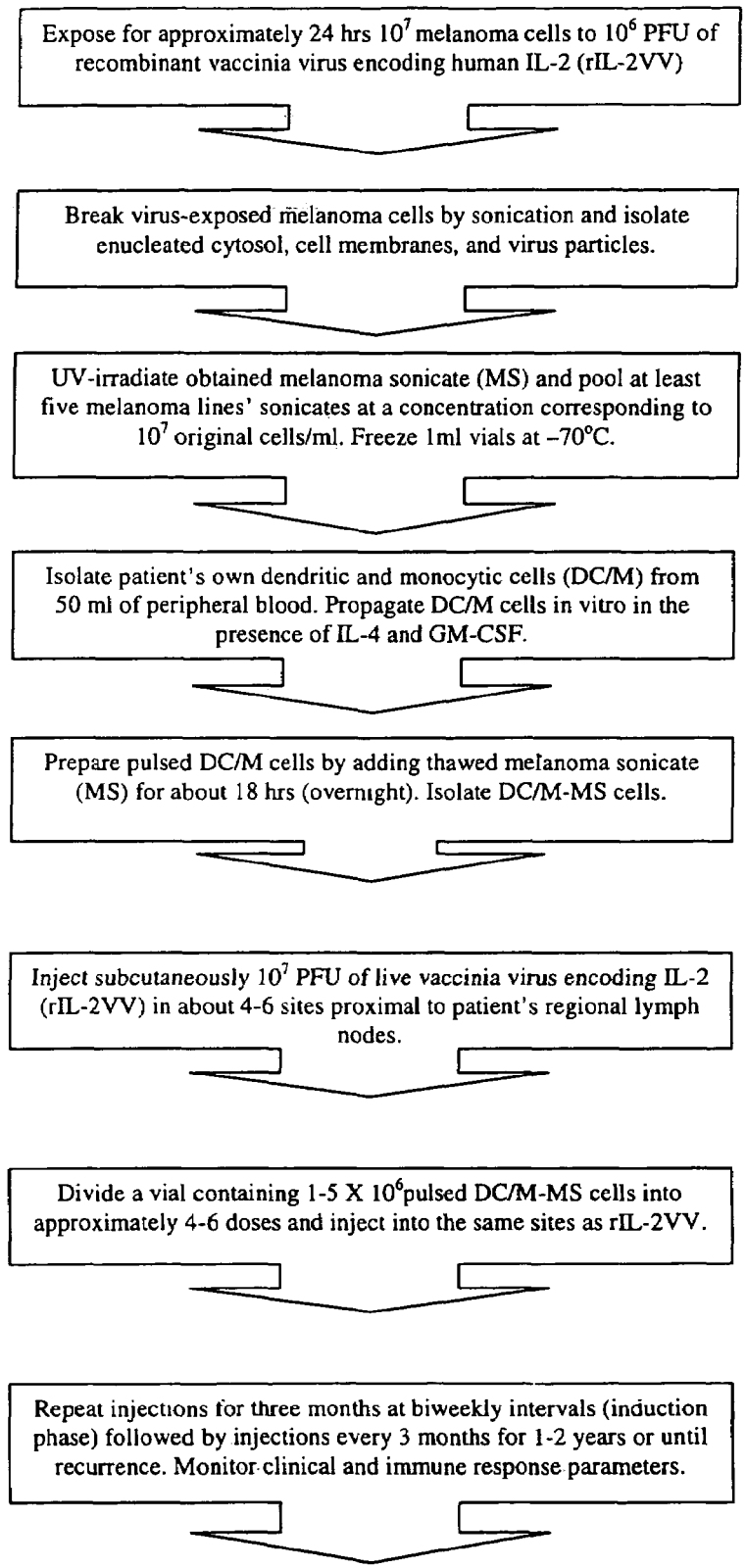
FIG. 1 is a flow chart illustrating the steps in the preparation of CVACII vaccine.

The present invention relates to an improved immunotherapeutic vaccine useful for treating a host diagnosed with cancer, e.g., melanoma, as well as methods of making and using the vaccine and various components of the vaccine.

The term "HLA" means human leukocyte antigen and is equivalent to the term "major histocompatibility complex" (MHC) molecule. In general, class 1 molecules are MHC-encoded peptides that are associated with $\beta$2-microglobulin, while class 2 molecules have two non-covalently associated MHC encoded peptides. Class 1 (HLA-A, B, C) and 2 (HLA-D or DR, DQ, DP) molecules, when on the cell surface, are capable of presenting "antigens" or "immunogens"-molecules which elicit an immune response. The term "immune response" is commonly associated with the activation of immune cells. However, the opposite is true as well when an immunogen causes immune tolerance or anergy. The term "HLA-matched" means those HLA antigens from one individual are essentially similar to HLA antigens from another individual.

The term "autologous cells" means that the cells are an individual's own cells. Dendritic cells (DC) are one subtype of "antigen presenting cells" (APC) capable of eliciting an immune response or reaction mediated in part by "cytotoxic T lymphocytes" (CTL). CTL are cells capable of killing or suppressing the growth of cells having response-eliciting antigens. The term "CTL" usually refers to CD8+ T-cells, although CD4+ T-cells and "natural killer" (NK) cells can also display cytolytic activity. When CTL are activated or primed with lymphokines such as IL-2 they are also called lymphokine activated killer cells or "LAK" cells. The term CD, e.g., CD8 or CD4, stands for cluster of differentiation and usually represents an immune marker used to distinguish different types of cells. The term "antigen presenting cells" usually means specialized lymphoid cells such as dendritic cells, B cells, and monocytic cells, which are capable to induce T cell activation. The term "monocytes" refers to cells related to "macrophages" and they represent yet another type of APC, which mainly re-activate previously sensitized CTL. DC, however, appear to activate functionally-native or unprimed T cells. Both DC and monocytes are needed to activate and to sustain immune cell responses. In addition to differences in immune phenotype, these two types of APC differ morphologically, DC having more pronounced "hairy" or "dendritic" phenotype. However, in contrast to monocytes, the exact origin of DC is still unclear as they can be obtained from a variety of tissues, e.g., peripheral blood, spleen, thymus, bone marrow, lymph nodes, or skin. Monocytes can be obtained essentially from the same sources. Some DC are also known as "veiled" cells found in the blood or as "Langerhans cells" usually found in the epidermis.

The term "immunostimulating molecule" refers to cytokines, hematopoietic growth factors, and melanoma immunogens. The term "cytokine" refers to bioactive molecules derived from cells and capable of affecting cells' behavior, e.g., growth, migration, killing capacity, differentiation, secretion, etc. The term "lymphokine" means essentially same as the cytokine but usually refers to bioactive molecules derived from lymphocytes and affecting predominantly the behavior of lymphocytes.

The term "immunotherapeutic vaccine," as opposed to the notion of a "prophylactic vaccine," means a vaccine administered to treat and/or prevent further progression of the disease in a host already diagnosed with the disease. The term "administering" means any method of providing a host in need thereof with a vaccine, including oral, intranasal, topical, transdermal, parenteral, e.g., intravenous, subcutaneous, intradermal, intramuscular, and other means of delivery known in the art.

The term "melanoma" means a malignant skin cancer or tumor of varying degree of severity and having the tendency to spread or "metastasize" in advanced stages of the disease. The term "cancer" or "neoplasm" generally means a malignant disease and is characterized by an uncontrolled growth of "tumor" or cancer cells. Tumors may spread locally as a primary tumor mass or spread to the distant parts of the body, i.e., metastasize.

The term "enucleated cytosol" refers to the cytoplasmic contents of a cell from which the nucleus has been removed with minimal rupture of the nucleus. Hence, enucleated cytosol is substantially free of nuclei. As used herein, "pulsing" means to provide an antigen presenting cell with an antigen, or an immunogen, or a preparation containing antigens or immunogens, e.g., such as a preparation of tumor antigens derived from a tumor. In a preferred embodiment, antigens, immunogens, or a preparation is bound to or taken up by the APC, for processing into peptides to be delivered to the plasma membrane as a peptide-MHC or peptide-HLA complex. When this complex is contacted by an immune cell, e.g., CTL, it will prime these cells to recognize and kill tumor cells carrying a similar antigen or immunogen. By pulsing APC with tumor antigens, the immunogenicity of these antigens is improved.

The term "CVACII vaccine" encompasses two components: the first is a live recombinant vaccinia virus encoding a cytokine, e.g., human IL-2 (rIL-2VV), which is preferably injected first, and the second component comprises dendritic and/or monocyte cells (DC/M) pulsed with cancer and/or melanoma antigens derived from cancer and/or melanoma cells or cell lines exposed to a vaccinia virus encoding a cytokine, e.g., rIL-2VV. The second component is preferably administered about 30 minutes after rIL-2VV. The term "VV" stands for vaccinia virus and term "rVV" stands for recombinant vaccinia virus, which encodes an extraneous gene foreign to said virus.

The term "vaccine" as used herein includes a therapeutic or immunotherapeutic vaccine. In an embodiment of the invention, the vaccine is used in a host already diagnosed with cancer and can be administered to stimulate an immune response against a poorly immunogenic tumor. The immune response can lead to reduced tumor growth and spread, elimination of tumor cells by cellular and humoral immune responses, and/or prevention or delay of tumor recurrence upon partial or complete remission of the cancer.

One aspect of the invention is directed to a therapeutic composition of antigen presenting cells pulsed with a preparation of tumor antigens found in an enucleated cytosol and cell membranes of cancer cells, e.g., melanoma cell lines, which were non-cytolytically infected with recombinant vaccinia virus encoding an immunostimulating molecule, e.g. such as a cytokine, IL-2, a hematopoietic factor, or a tumor immunogen. In a preferred embodiment the APC are the host's own or HLA-matched antigen presenting cells, e.g., dendritic and/or monocytic cells. The composition may contain cancer cell membranes containing at least two and preferably more than two HLA class I A antigens. In a preferred embodiment of the invention melanoma cells such as Mel-2, Mel-3, Mel-4, Mel-6, and Mel-9 melanoma cell lines are used. HLA-matched dendritic and/or monocytic cells provided by a donor are also contemplated as useful constituents of this vaccine.

The instant invention is directed to administering rVV encoding at least one immunostimulating molecule such as a cytokine, a hematopoietic growth factor or a melanoma immunogen. The present invention contemplates that the vaccinia virus includes genes encoding cytokines and hematopoietic growth factors such as FLT-3 or FLT-3/FLK-2 ligand, GM-CSF, G-CSF, IL-2, IL-3, IL-4, IL-6, IL-7, IL-12, IL-15, IL-18, stem cell factor, various interferons, or a combination thereof. The practitioner will appreciate that these cytokines can stimulate the immune system of a host in a manner similar to IL-2 action.

The present invention also contemplates the use of recombinant vaccinia virus encoding melanoma immunogens such as MAGE-1, MAGE-3, BAGE, GAGE, PRAME and NY-ESO-1 antigens; melanocyte differentiation antigens such as tyrosinase, Melan-A/MART-1, gp100, TRP-1 and TRP-2; mutated or aberrantly expressed antigens such MUM-1, CDK4, beta-catenin, gp100-in 4, p. 15 and N-acetylglucosaminyltransferase; and other suitable antigens like B7-1, TA-90, lysosome-associated membrane protein (LAMP), melanocyte-stimulating hormone receptor (MCIR), p90 calnexin, and other antigens known in the art. These immunogens or antigens may provide further benefit in the instant composition by adding an additional challenge(s) to a host's immune response.

A preferred embodiment of the present invention is termed CVACII. In this embodiment the vaccinia virus (VV) used is a recombinant virus containing a gene encoding human IL-2. In addition, the APC in the CVACII embodiment are preferably pulsed with preparations from any one of five human melanoma cell lines or cell lines expressing more than one HLA class I A antigen. Finally, the patient's own dendritic cells as well as monocytes can be used as APC in CVACII.

Although the embodiment exemplified herein encompasses melanoma therapy, one skilled in the art would recognize that the principles disclosed are equally applicable to a variety of other malignant tumors including but not limited to squamous cell carcinoma, lung cancers, breast cancers, head and neck carcinomas, thyroid carcinomas, soft tissue sarcomas, bone sarcomas, testicular cancers, prostatic cancers, ovarian cancers, bladder cancers, other types of skin cancers, brain cancers, angiosarcomas, mast cell tumors, primary hepatic cancers, pancreatic cancers, gastrointestinal cancers, renal cell carcinomas, lymphomas, and hematopoietic neoplasias.

Although preferred cells for use in human melanoma vaccines are from the Mel-series (e.g., Mel-2, Mel-3, Mel-4, Mel-6, Mel-9), other melanoma cell lines can be used. Such cell lines can be established de novo from tumor biopsies of melanoma patients or can be selected from already existing sources. For example, cell lines designated as FM3, FM6, FM9, FM28, FM37, FM45, FM55p, FM55M1 and FM55M2 were established by Kirkin et al. from eight metastatic tumors and one primary tumor of seven different patients (Kirkin, A. F., Petersen, T. R., Olsen, A. C., Li, L., thor Straten, P., Zeuthen, J. Generation of human-melanoma-specific T lymphocyte clones defining novel cytolytic targets with panels of newly established melanoma cell lines, Cancer Immunol. Immunother. 41(2):71–81, 1995). Procedures for establishing melanoma lines are routine and well known by those of ordinary skill in the art. It will be appreciated that similar method will be applicable to the selection or establishment of transformed cell lines corresponding to tumors and cancer cells of other cell types. It will also be appreciated that where common tumor antigens are involved, vaccines can be developed from cell lines which are of different origin that the cancer to be treated.

In preferred embodiments of the present invention the selected melanoma cell lines provide at least two HLA class I antigens, preferably HLA-A2 and/or A1. In general, HLA-A2 expression is predominant in melanoma patients and plays the critical role in HLA class I restricted CTL killing of melanomas. However, some patients may express other HLA alleles. Accordingly, melanoma cell lines should preferably express more than above two HLA antigens. More preferably they should express a third HLA-A antigen and preferably this antigen is A3 antigen.

In a preferred embodiment of the instant invention, the DC are used in combination with other types of antigen presenting cells such as monocytes (M). It is preferable that DC/M cells are used freshly although one can freeze them according to established methods (e.g., U.S. Pat. No. 5,788,963) and use them whenever it is necessary. According to a preferred embodiment, DC/M cells are obtained from a patient's own blood. According to another embodiment DC/M cells are obtained from an HLA-matched donor. In addition to melanoma therapy, the instant invention provides a method of treating metastatic melanoma especially those affecting lung, liver, brain, and being either cutaneous or subcutaneous. The instant invention is also applicable to other types of cancer. In a preferred embodiment, these types of cancer may comprise fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, Kaposi's sarcoma, medulloblastoma, craniopharyngioma, ependymoma, pinealoma, hemangioblastoma, acoustic neuroma, oligodendroglioma, meningioma, neuroblastoma, retinoblastoma, myeloma, lymphoma, or leukemia. Accordingly DC/M cells can be prepared from patients suffering from above types of cancer and are pulsed with corresponding tumor antigens which can be obtained from a patient's own tumor or from established cell lines of the same type as the tumor in need of therapy.

In embodiments of the invention, extracts for use in pulsing of DC/M cells are prepared from transformed cell lines which have been infected with recombinant vaccinia virus. Preferred extracts are those from which nuclear material has been removed so that the preparations comprise enucleated cytosol and cell membranes from recombinant or vaccinia virus infected cells. For example, a cell suspension of melanoma cells is exposed to a rIL-2VV preparation at a ratio of about 10 cells to about 1 PFU of the rIL-2VV. In accordance with the invention, the ratio of cancer cells to virus can vary and can be anywhere between about 1000–0.001 cells to about 1 PFU of virus. After a short incubation period, to avoid virus-induced cell lysis, preferably 4–36 hrs, more preferably 18–30 hrs and even more preferably 24 hrs in a $CO_2$ incubator, the melanoma cells are separated from the culture supernatant. This can be accomplished, for example, by spinning at approximately 1,200 rpm for 10 min in a refrigerated centrifuge. Other means of separating cells and culture medium are well known in the art and can be employed. The separated melanoma cells are collected and disrupted by mechanical, chemical or physical means. A variety of methods are known and can be employed. These can include repeated freezing and thawing, high pressure (French press), Dounce homogenizer, microwave or ultrasound irradiation, various detergents, or any other methods known in the art. The preferred method is a high frequency vibration or sonication method using a probe sonicator. In preferred embodiments of the invention, cells are disrupted but nuclei remain substantially intact. The condition of the disrupted cells is monitored, for example, with a microscope. The disrupted cells are then treated to remove nuclei, for example, by centrifugation at 800 rpm for 10 min. The remaining cellular material comprises vaccinia virus particles, enucleated cytosol and cell membranes, and is used for pulsing of DC/M. In an embodiment where sonication is employed to disrupt cells, the cellular material is the melanoma sonicate (MS). In certain embodiments of the invention, the virus collected from the culture supernatant is added back to the cellular material before pulsing of DC/M. In a preferred embodiment, the combination of MS and recombinant virus from the supernatant is referred to as rIL-2VV-MS. Prior to pulsing of DC/M, the MS or rIL-2VV-MS can be further treated to inactivate virus particles, for example, by exposure to ultraviolet light.

Pulsing of DC/M involves contacting DC/M with the cellular material recovered from the disrupted cells. In a preferred embodiment, contacting is for a period of time sufficient for processing and presentation of tumor and vaccinia virus antigens by the DC/M. Methods for pulsing immune system cells for presentation of antigen are well known to those of skill in the art.

Preferably, antigen presenting cells are obtained from the patient. The use of a patient's own or autologous APC and preferably DC, provides an opportunity for devising an individualized therapeutic approach. (Celluzzi, C. M., Falo, L. D. Jr. Physical interaction between dendritic cells and tumor cells results in an immunogen that induces protective and therapeutic tumor rejection. J. Immunol. 160(7):3081–3085, 1998).

A method of making the instant composition is also disclosed. In a preferred method, the composition is prepared by growing tumor cells or tumor cell lines as the source of enucleated cytosol and cell membranes; contacting the cells with a recombinant vaccinia virus encoding an immunostimulating molecule, e.g., IL-2, in a serum free medium; sonicating or disrupting substantially intact vaccinia-infected cells to cause cells' break-down (cell sonicate); spinning cell debris to separate from cell nuclei; collecting the sonicate containing enucleated cytosol, vaccinia virus, and cell membranes; inactivating, e.g., irradiating the sonicate with ultraviolet light; pooling more or less equal volumes of sonicates from different tumor cells; adjusting the volume of sonicate to about ten million original cells per ml; dispensing each 1 ml volume of pooled sonicate into sterile glass vials; freezing and storing said vials at −70° C.; retrieving dendritic and/or monocyte cells from an HLA-matched donor or from a host diagnosed with a cancer and growing said cells in culture (ex vivo); mixing or pulsing dendritic and/or monocytic cells with thawed supernatant of cancer cells in a serum free medium; and collecting pulsed dendritic and/or monocytic cells.

It is preferable that the DC/M are administered from freshly prepared cells. However, one can freeze the cells according to techniques well known in the art (U.S. Pat. No. 5,788,963) and subsequently use the DC/M when needed.

In another embodiment, the invention provides a method for eliciting an anti-cancer immune response, comprising administering, to a host diagnosed with a cancer, an effective amount of a live recombinant vaccinia virus encoding an immunostimulatory molecule, such as a cytokine, e.g., IL-2, and an effective amount of antigen-presenting cells. Prior to administration antigen-presenting cells are pulsed with an enucleated cytosol and cell membranes from cancer cells infected with a recombinant vaccinia virus encoding the same or another immunostimulatory molecule.

Also contemplated by the invention, is a method for treating a human host diagnosed with a cancer, e.g., melanoma by administering, preferably subcutaneously (s.c.), a live recombinant vaccinia virus encoding an immunostimulatory molecule such as a cytokine, e.g., IL-2, and injecting, preferably into substantially the same site, a therapeutic composition prepared in accordance with the instant invention.

In a preferred embodiment the effective amount of a live recombinant vaccinia virus encoding an immunostimulating molecule comprises an amount ranging from $10^4$ to $10^9$ plaque forming units (PFU) per injection. Preferably, effective amounts are between about $10^5$ and $10^8$ PFU, and more preferably about $10^7$ PFU. Generally, the effective amount of therapeutic composition comprises an amount in a range about from $10^5$ to $10^9$ original cancer cells per injection. Preferably, the effective amount is between about $10^6$ and $10^8$ cells, and more preferably about $10^7$ cancer cells. The preferred number of antigen presenting cells (APC) in one dose of a vaccine is about 1 to 5 million cells. The ratio between cancer cells and plaque forming units (PFU) of recombinant vaccinia virus is selected from the range of about 1,000–1 cancer cells to about 0.001–1 of PFU. Preferably the ratio between cancer cells and PFU of recombinant vaccinia virus is about 10 to about 1. In turn, the ratio between cancer cells and antigen presenting cells is selected from the range of about 1,000–1 cancer cells to about 10–1 antigen presenting cells. The preferable ratio between cancer cells and antigen presenting cells is about 10 cancer cells to 1–5 APC.

It is preferable that the instant immunotherapeutic vaccine is administered subcutaneously or intradermally for a period of time and in an amount necessary to provide the therapeutic effect. Accordingly, preferred sites of the injection are on anterior thighs, anterior upper arms, or the anterior thorax. The minimum duration time of the vaccine therapy is at least one day, preferably at least three months, more preferably at least one year or longer and even more preferably until disease remission or disease recurrence. Therapy can also continue after disease recurrence if considered beneficial to the host. In this case, changing tumor antigens may be desired and is contemplated.

In preferred embodiments of the invention, DC/M-rIL-2VV-CS can be injected intradermally or subcutaneously into sites near to regional lymph node groups. Each injection can be equally divided among at least 4 to 6 injection sites—at least 2 to 4 above the waist and at least 2 below the waist near inguinal nodes. In a preferred embodiment, rIL-2VV is injected first, and the DC/M-MS is injected about 30 min. later at approximately the same sites. Other routes of administration are envisioned and can include continuous (such as intravenous drip), intramuscular, transdermal (which may include a penetration enhancement agent), sustained release by encapsulating into delivery vehicles such as liposomes.

Preferably, immunization with a composition of the invention is performed using multiple injections administered over a time course which is selected to maximize an immune response. In a preferred embodiment, melanoma patients receive six biweekly injections for 12 weeks, then every three months for 2 years or until cancer recurrence. However, any suitable immunization regimen can be used. One of ordinary skill can modify methods of administration within the teachings of the specification to provide numerous routes without rendering the composition of the present invention unusable or compromising its therapeutic value.

The DC/M obtained are used in DC/M-MS preparation and also for in vitro studies to determine immune activation signs.

Biopsies can be taken for determination of IL-2 production or production of any other immunostimulatory molecule by methods known in the art.

The following Examples are presented to illustrate the present invention. These examples are not intended in any way to otherwise limit the scope of the disclosure.

EXAMPLES

Example I

Preparation and Testing of a Prototype CVACII Vaccine in a Murine Model

Cell Lines

Murine colon cancer cell line CC-36, human fibroblast cell line MRC5, monkey kidney cell line VERO, NK sensitive cell line YAC-1, murine anti-CD4 antibody secreting cell line GK1.5, murine anti-CD8 secreting cell line TIB210-2.43, IL-2 dependent cell line CTLL, thymidine kinase negative cell line 143B were obtained from ATCC and maintained in either EMEM or RPMI media with appropriate nutrients.

Mice

Balb/C mice of 4–6 weeks old were used in all the therapeutic cancer vaccine experiments, and for the isolation of dendritic cells, and for the preparation of anti-CD4 or anti-CD8 monoclonal antibody-containing ascites.

Vaccinia Virus (VV)

A recombinant vaccinia virus (rVV) was prepared with a complete *Escherichia coli* β-galactosidase gene (lacZ) and another rVV having the human IL-2 gene (rIL-2VV) inserted into the same locus as the lacZ gene of rVV. These viruses were expanded in either MRC5 or VERO cells and quantified by a plaque-forming assay using VERO cells. The method of preparation of rIL-2VV is described by Flexner et al. (Flexner C, Hugin A, Moss B. Prevention of vaccinia virus infection in immunodeficient mice by vector-directed IL-2 expression, Nature 330:259–262, 1987).

Vaccinia Colon Sonicate (rIL-2VV-CS) Preparation

Vaccinia colon sonicate using rIL-2VV is prepared by a modified method as described. (Sivanandham, et al., Cancer Immunol. Immunother. 38:259–264, 1994). Briefly, CC-36 cells were co-cultured for 24 hours with rIL-2VV at a ratio of one cell to one PFU of virus. Vaccinia virus-infected CC-36 cells were then collected, separated by centrifugation, and broken by sonication. Cell nuclei were removed from the sonicate by centrifugation at 800 rpm for 10 minutes. Vaccinia virus and tumor cell debris were isolated from the cell/virus co-culture supernatant by centrifugation at 100,000×g for 1 hour and mixed with the cell sonicate. The resultant suspension was exposed to short wave UV for 1 hour to inactivate virus and then aliquoted and stored at −70° C. until use. Aliquots contained about $10^6$ cell equivalents in 0.2 ml of saline (0.9% sodium chloride).

Analysis of the Production of IL-2 from the rIL-2VV

IL-2 was measured in culture supernatants of rIL-2VV-infected CC-36 cells and in sera of mice injected with rIL-2VV using commercial ELISA kits and by a suitable bioassay. The kinetics of the production of IL-2 were tested both in vitro and in vivo procedures.

Preparation of Spleen-Derived Dendritic/Monocytic Cells

Dendritic and monocytic (DC/M) cells were isolated from spleens from the same mouse strain. The spleens were minced on a wire mesh and all dissociated cells were collected in Hank's balanced salt solution (HBSS). These cells were overlaid on Ficoll-Hypaque and centrifuged at 400 g for 30 minutes, harvested from the Ficoll-Hypaque interface, washed twice in HBSS, counted in trypan blue, and then resuspended in complete RPMI medium. The cells were allowed to adhere to the plastic surface of a tissue culture dish for 1–2 hours. Non-adherent cells were removed by 4 washes with medium. The adherent cells contained predominantly macrophages/monocytes and dendritic cells. Cells were kept overnight in RPMI 1640 complete medium. The following day, floating cells were removed, washed with HBSS and kept in complete RPMI medium containing 2000 units of murine GM-CSF and 1,000 units of murine IL-4. These cytokines favor predominantly the growth of DC. However, some monocytic cells are also found in the culture. After culturing for five days, DC/M cells were harvested, washed twice with PBS and then pulsed with rIL-2VV-CS as follows. One million DC/M were incubated in 5 ml of FBS free RPMI medium with the contents of one vial (about $10^6$ cell equivalents) of rIL-2VV-CS. Thus, pulsing involved a mixture containing approximately one DC/M cell to one cell equivalent of rIL-2VV-CS. The mixture was incubated overnight at 37° C. with rocking. The next day, pulsed DC/M cells were spun down and washed with HBSS twice.

Experimental Design

Solid tumors were induced in mice by injecting $10^4$ CC-36 cells in 100–200 μl of HBSS at the right flank region, and the efficacy of the rIL-2VV+DC/M-rIL-2VV-CS combination therapy was studied. Eight groups of 10 mice were used in this experiment. Group I was treated with rIL-2VV+DC/M-IL-2VV-CS (CVACII); Group II was treated with a control VV+DCIM-VV-CS; Group III was treated with DC/M-rIL-2VV-CS; Group IV was treated with DC/M-VV-CS; Group V was treated with DC/M-CC-36 lysate (i.e., crude cell lysate as used in the prior art methods); Group VI was treated with rIL-2VV; Group VII was treated with a non-recombinant VV control; and Group VIII had no treatment. These groups, as treated with respective vaccines are shown in Table 1.

TABLE 1

Treatments Administered

| | |
|---|---|
| Group I | rIL-2VV + DC/M-rIL-2VV-CS |
| Group II | VV + DC/M-VV-CS |
| Group III | DC/M-rIL-2VV-CS |
| Group IV | DC/M-VV-CS |
| Group V | DC/M-CC-36 lysate |
| Group VI | rIL-2VV |
| Group VII | VV |
| Group VIII | None |

In the first and second groups, the administration was carried out in two steps. First, one million PFU of viable rIL-2VV or control "wild-type" VV in 100 μl was injected subcutaneously in the left flank region. Thirty minutes later, DC/M-rIL-2VV-CS or DC/M-VV-CS in 200 μl was injected at the same site. Mice received injections on day 4, 10, and 17 after the tumor transplantation.

To determine the efficacy of vaccine preparations, the mice were observed for tumor incidence. Tumor incidence and diameter was measured at 2–3 days interval to assess tumor growth. The effect of the treatments on survival was also determined.

Analysis of the Induction of Tumor Specific Immunity

Sera and lymphocytes from mice of different treatment groups were collected and used in the suitable in vitro analysis to demonstrate the induction of anti-CC-36 immune responses. Cellular assays were performed using peripheral blood lymphocytes (PBL) or splenic lymphocytes of mice from the different groups. Lymphocytes were prepared from peripheral blood or spleen by standard methodology.

Cytolytic Assays

CC-36 specific cytolytic activity of PBL or splenic lymphocytes was measured using a standard chromium release assay. Freshly prepared lymphocytes were co-cultured with irradiated rIL2-VV-CS pulsed DC/M for 5 days to 2 weeks in RPMI medium containing 10 units of interleukin-2. CC-36 or YAC-1 target cells were harvested, washed and incubated with 100 μCi sodium chromate/$10^6$ cells ($^{51}$Cr, Amersham), in 0.5 ml volume for 60 minutes at 37° C. After washing with RPMI 1640 four times, radiolabelled target cells were added at $10^4$/ml in 100 μl volume to conical microtiter plates (Costar). Effector lymphocyte to target tumor cell ratios (E:T) were in a range of 100:1–10:1. E:T were used in quadruplicate wells. Plates were spun at 250 g for 5 minutes and incubated at 37° C. in a humidified incubator containing 5% $CO_2$. After four hours, the supernatants from the wells were harvested on fiber filters utilizing a Skatron Collection System and counted for one minute on a gamma counter. To determine maximum $^{51}$Cr release, 0.1 ml of 1% sodium dodecyl sulfate solution was added to appropriate wells. Counts per minute (cpm) were used to calculate percent release (% R) according to the formula:

$$\% R = \frac{\text{experimental release} - \text{spontaneous release}}{\text{maximum release} - \text{spontaneous release}} \times 100$$

CTL Precursor Frequency (CTLp) Assay

Fresh lymphocytes were isolated from mice from the above treatment groups. 2–10×$10^4$ lymphocytes in 50 μl of medium containing 50 units/ml of recombinant IL-2 were added to each well with $10^3$ CC-36 sonicate-pulsed DC/M.

At least 50 replicates were used in this test. The co-cultures are kept for 21 days in a humidified $CO_2$ incubator. On day 6, 12, and 18, 50 µl of fresh medium was added to each well. On day 21, about $10^3$ YAC-1 cells were added followed by $10^3$ $^{51}$Cr-labeled CC-36 cells. After four hours, supernatants were harvested and counted using a gamma counter. Positive wells were those showing greater than 10% cytotoxicity in comparison to the control wells.

ELISA Measuring the Induction of Antibody to CC-36 Tumor

ELISA plates were coated with 10 µg/well of CC-36 tumor cell sonicate in bicarbonate buffer (pH 9.4). Unbound sites capable of non-specific binding were blocked with 1% human serum albumin and incubated overnight at 4° C. 100 µl of diluted serum from immunized mice were added per well and incubated at 4° C. overnight. Assays included a negative control using normal mouse serum. Plates were washed three times with PBS. 100 µl of a 1:1000 dilution of biotinylated goat anti-mouse second antibody (Sigma, St. Louis, Mo.) was added to each well. After incubation at 37° C. for 1 hour, plates were washed three times with PBS and incubated with 100 µl of avidin-alkaline phosphatase conjugate (Sigma, St. Louis, Mo.) (1:1000 dilution) for 30 min. The plates were washed three times with PBS and 100 µl of p-nitrophenyl phosphate (PNPP; Sigma, St. Louis, Mo.) substrate was added. After 30 minutes, the reaction was stopped by addition of 50 µl of 3 M sodium hydroxide per well. $OD_{406}$ values obtained from the ELISA assay indicated the titer of anti-tumor antibodies.

Statistical Analysis

A statistical prediction was used to find the total number of animals (10) required per treatment group to produce a 30–40% difference in treatment arm in favor of the new cancer vaccine treatment with an 85% confidence interval. Student's T test and Wilcoxon survival analysis or log-rank survival analysis was used to determine the difference between groups of vaccines.

Results

Figure 2:
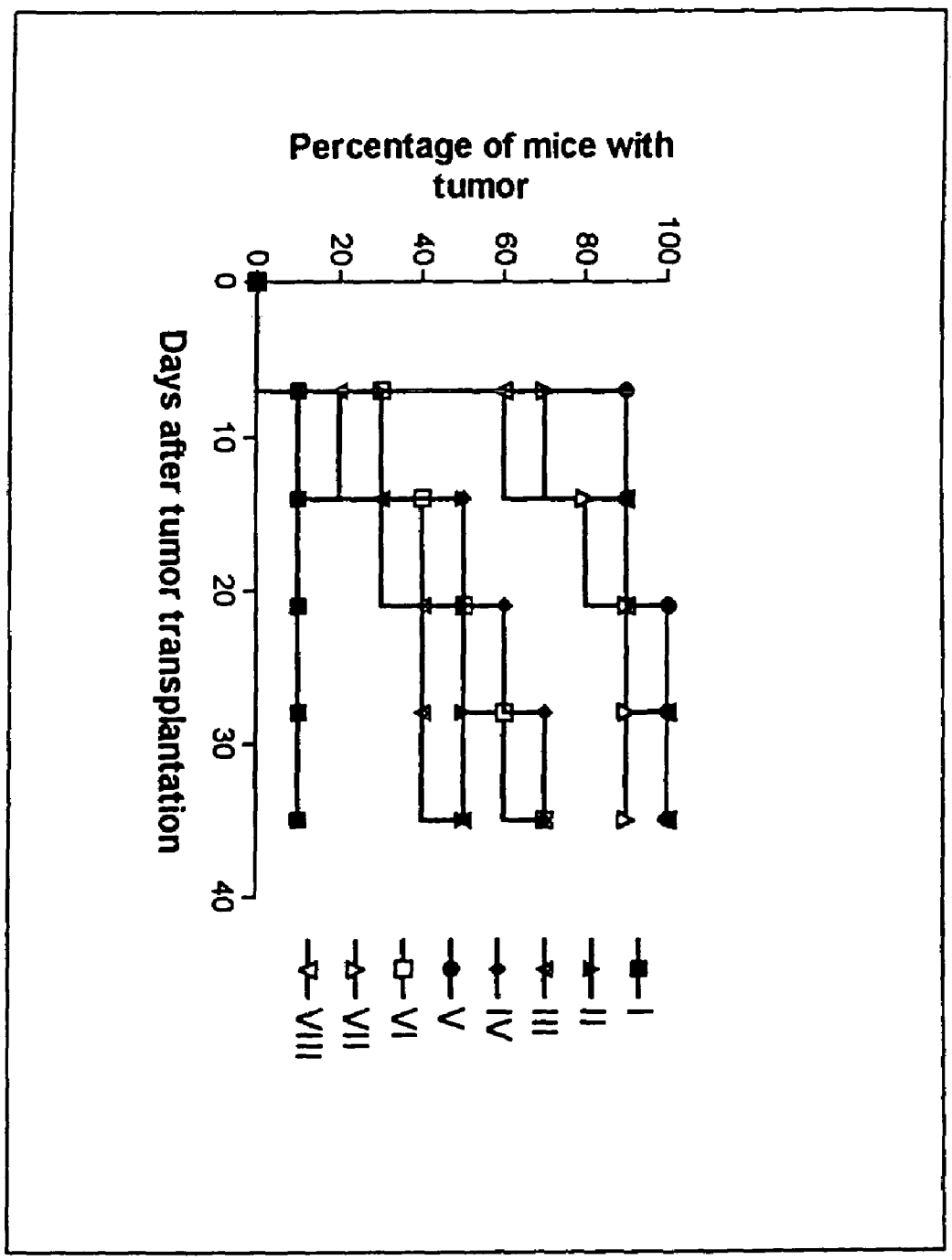
FIG. 2 shows relative efficacy of various vaccine preparations in protecting against development of tumor.
Figure 3:
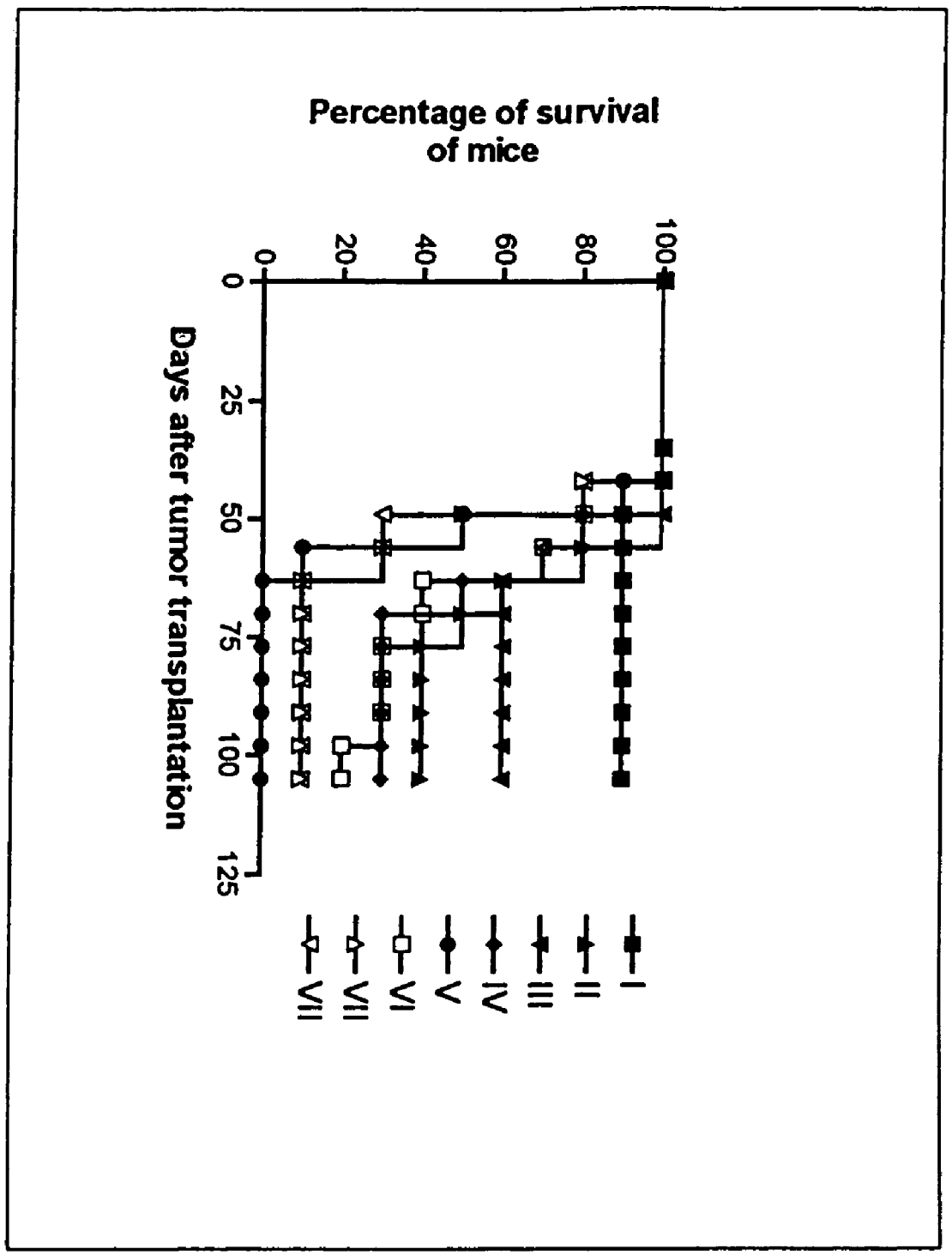
FIG. 3 shows percent of survival of mice treated with seven different vaccine preparations and with a no-treatment protocol.

Four separate experiments were performed in this murine model study. FIG. 2 shows the efficacy of the various vaccine preparations on incidence of tumors of 5±2 mm mean diameter during the 30 days following tumor implantation. Only one mouse in the CVACII vaccine group (group I) developed tumor (10%). In other groups, the tumor incidence observed during the 30-day period was 50–100%. Thus, tumor incidence was significantly reduced in group I as compared to other groups (p<0.05). Group V represents mice which were treated with a typical DC-based vaccine. In addition, a survival experiment was performed using the same treatment groups and the same tumor induction protocol. An autopsy was performed on each mouse to identify the cause of death. The results are represented in the FIG. 3. In this survival study, 90% of mice that received rIL-2VV+DC/M-rIL-2VV-CS (CVACII) treatment survived beyond 100 days following tumor transplantation. The survival rate for mice in the other groups was 0–60%. Thus, when compared with other treatments the rIL-2VV+DC/M-rIL-2VV-CS treatment produced a significantly better survival rate (p<0.05). The results shown in FIGS. 2 and 3, indicate that rIL-2VV+DC/M-rIL-2VV-CS therapy induces a significant and durable anti-tumor response.

Figure 4:
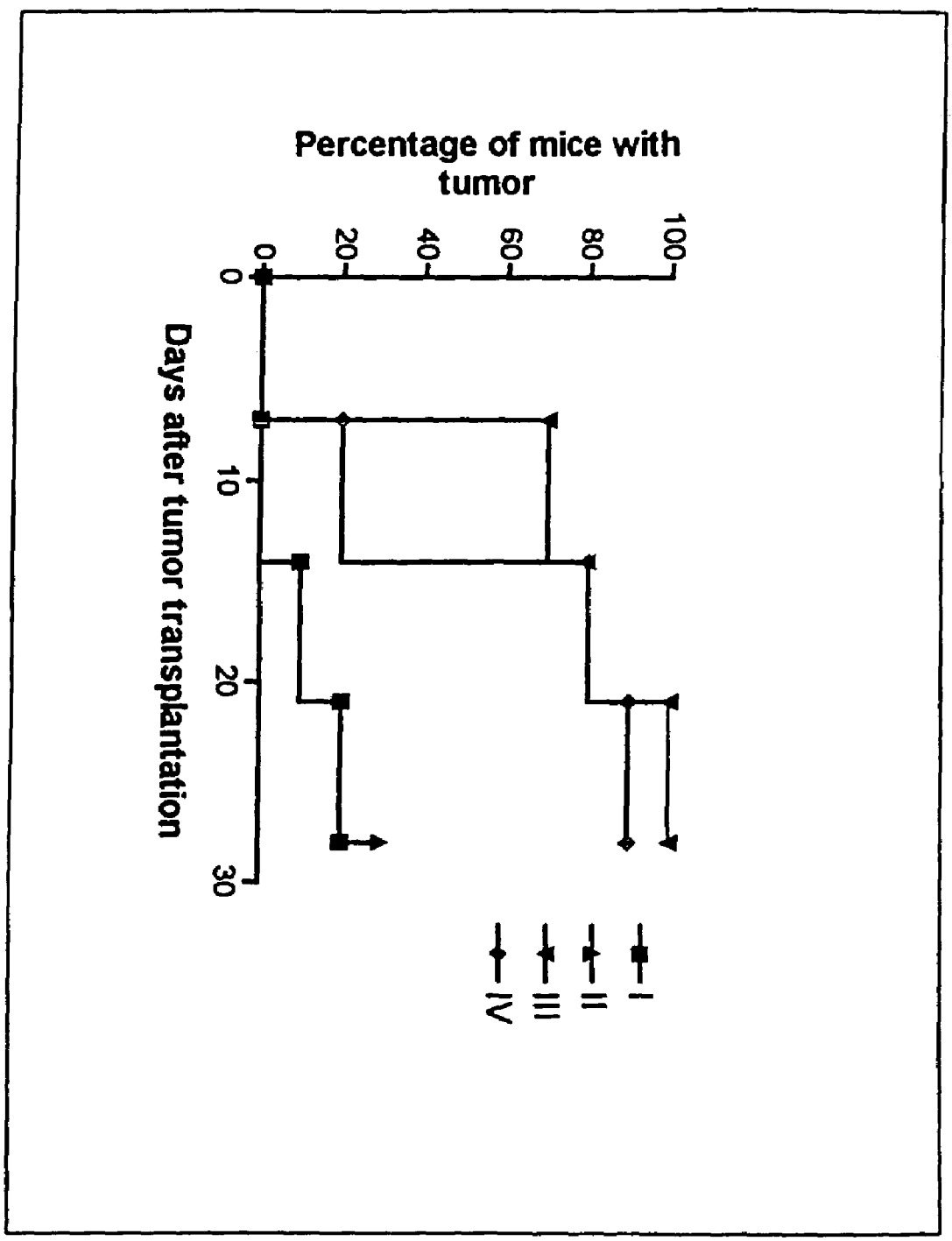
FIG. 4 demonstrates that vaccine protection correlates with induction of CD8-positive cytolytic cells.
Figure 5:
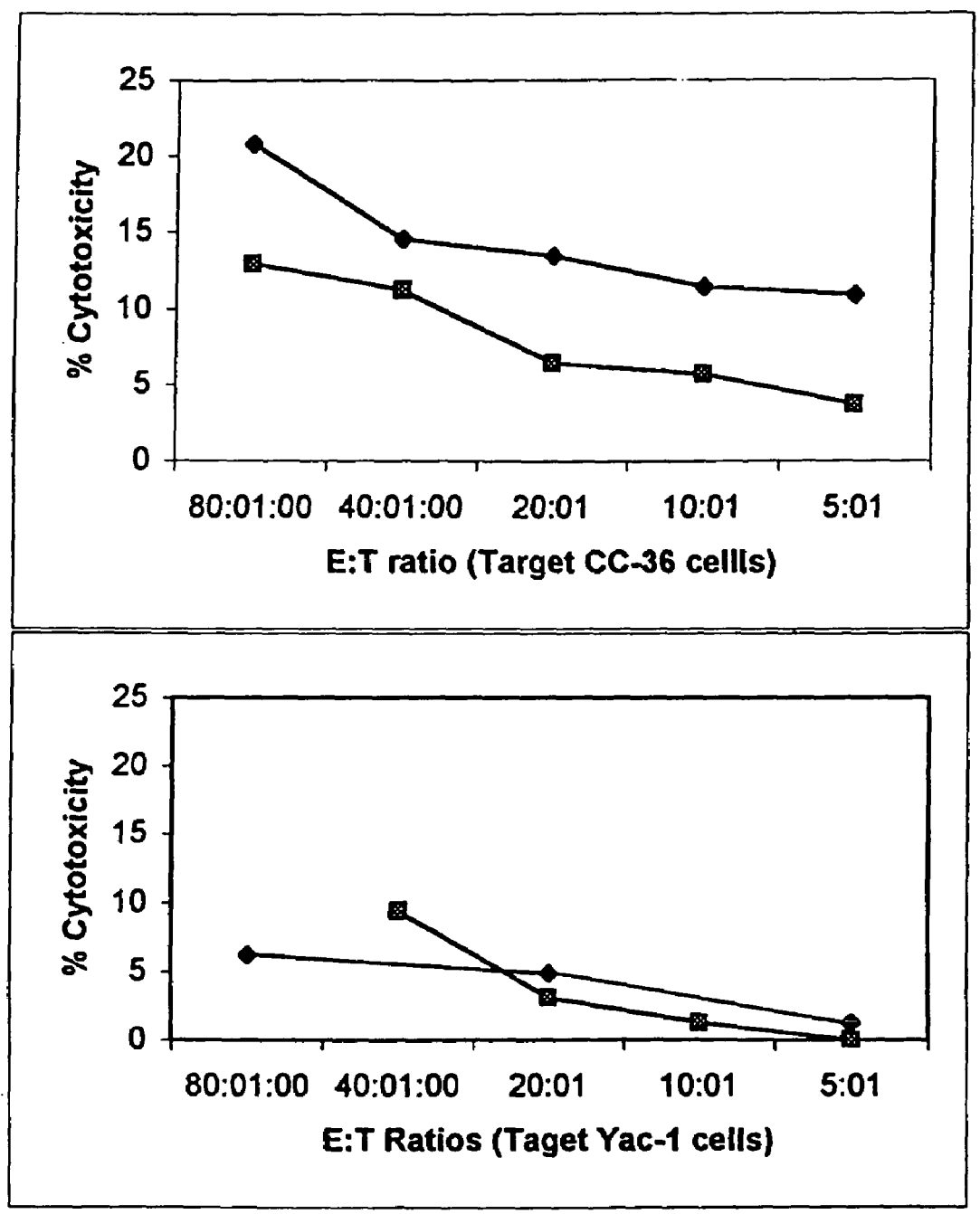
FIG. 5 shows cytotoxicity tests resulting from treatment with CVACII vaccine and control vaccine preparation consisting of DC/M pulsed with tumor sonicate only.

The mechanism of induction of anti-tumor response by rIL-2VV+DC/M-rIL-2W-CS therapy was evaluated in vivo using mice depleted in either CD4$^+$ helper T cells or CD8$^+$ cytolytic T cells (FIG. 4) and in vitro using PBL from mice treated with rIL2-VV+DC/M-rIL-2VV-CS (FIG. 5). On day 2 following tumor induction, mice in the group II were injected with 0.5 ml of anti-CD4 antibody-containing ascites and mice in the group III were injected with 0.5 ml of anti-CD8 antibody-containing ascites. Mice in group I, II and III were then treated with rIL-2VV+DC/M-rIL-2VV-CS on day 4, 11 and 18. Mice in group IV received no treatment following tumor induction. The incidence of tumor in each group was checked every 2–3 days and recorded. Groups I and II showed similar protection against tumor development. This protection is significantly higher than the tumor protection in groups III and IV. Mice depleted of CD4$^+$ helper T cells showed a level of protection against tumor similar to that of CD4$^+$/CD8$^+$ mice treated with rIL-2VV+rIL-2VV-CS. However, mice depleted of CD8$^+$ cytolytic T cells did not show any protection against tumor development in response to the IL-2VV+DC/M-rIL-2VV-CS therapy (FIG. 4). These results indicate that the anti-tumor response induced by the rIL-2VV+DC/M-rIL-2VV-CS is due to the induction of CD8$^+$ cytolytic T cells.

Analysis of PBL from mice treated with rIL-2VV+DC/M-rIL-2VV-CS therapy indicated a significantly higher cytotoxicity against CC-36 tumor (FIG. 5). Mice (n=20 per group) were treated with either CVACII or DC/M-CS (standard type DC vaccine; control) on day 1, 7 and 14. PBL were collected and stimulated with CVACII or control for 5 days in RPMI complete medium containing 10 units of rIL-2. PBL were then tested for cytotoxicity in a $^{51}$Cr release assay using CC-36 (FIG. 5, top panel) and YAC-1 (bottom panel) cells as targets at various effector to target ratios. PBLs from mice immunized with CVACII demonstrated greater cytotoxicity against CC-36 cells as compared with PBLs from mice immunized with the control vaccine. These results and the in vivo experiments support the involvement of CD8$^+$ positive cytolytic T cells in the anti-tumor response induced by CVACII therapy.

Example 2

Preparation and Clinical Testing of CVACII Melanoma Vaccine in Humans

Preparation and Administration of CVACII

Preparation and administration of CVACII to cancer patients involves the following steps: Preparation of clinical grade recombinant vaccinia virus encoding human interleukin-2 (rIL-2VV); Preparation of clinical grade melanoma cell lines derived from humans with metastatic melanoma; Incubation of rIL-2VV with melanoma cells for a sufficient period of time; Disruption of the melanoma cells by sonication and isolation of vaccinia virus, enucleated cytosol and cell membranes; Irradiation of the melanoma sonicate (MS) by UV in order to inactivate the virus; Preparation of dendritic/monocytic cells (DC/M) preferably from patient's own blood; Pulsing DC/M with melanoma sonicate to obtain a DC/M-MS preparation; Vaccinating a patient, first with rIL-2VV and then with the DC/M-MS preparation, preferably subcutaneously and preferably at the sites near regional lymph nodes.

Method of Administration

In the first step of a two step procedure, live rIL-2VV ($10^7$ PFU) was injected subcutaneously or intradermally into at least 4–6 sites near the regional lymph node groups. These sites were located on anterior thigh, upper arm, or anterior thorax. About thirty minutes later, DC/M-MS was injected at substantially the same sites as the initial rIL-2VV injection.

The vaccine was administered once every two weeks for three months and thereafter once every three months for one or two years or until recurrence or progression of disease.

Preparation of Recombinant Vaccinia Virus Encoding IL-2

Recombinant vaccinia virus encoding IL-2 (rVV-IL-2) was prepared using a clinical grade Wyeth strain vaccinia virus (a strain of virus similar to one used in the first generation VMO vaccine) and recombinant human IL-2 gene (pTCGF-11, No. 39673, ATCC, Manassas, Va.) by an established molecular methodology known in the art. The method of constructing a rVV is described in detail elsewhere (Sivanandham, M., Scoggin, D. S., Tanaka, N., Levi, M., Wallack, M. K., Therapeutic effect of a vaccinia colon oncolysate prepared with interleukin-2 gene encoded vaccinia virus studied in a syngeneic CC-36 murine colon hepatic metastasis model, Cancer Immunol. Immunother. 38:259–264, 1994; Lee, S. S., Eisenlohr, L. C., McCue, P. A., Mastrangelo, M. J., Lattime, E. C., Vaccinia virus vector mediated cytokine gene transfer for in vivo tumor immunotherapy, Proc. Am. Assoc. Can. Res. 1035:514, 1994). Briefly, a human cDNA clone specific for the IL-2 gene was isolated from a plasmid DNA encoding IL-2 using proper restriction enzymes. This IL-2 gene was blunt ended using a filling reaction and ligated into the SmaI restriction site in the tK gene segment of the plasmid pSC65.

The pSC65 plasmid containing the IL-2 gene and the Wyeth strain vaccinia vaccine virus (also containing tK gene in the non-essential region) was allowed to undergo homologous recombination in CV-1 cells as follows. First, a CV-1 cell monolayer was infected with the vaccinia vaccine virus (one cell to one PFU of virus) for 2 hours. The plasmid DNA encoding IL-2 was then transduced into these cells using a calcium chloride method. Five (5) ml of culture medium was added to the CV-1 cell culture followed by incubation for 3 hours. The medium was removed and 5 ml of fresh medium was added. The cell culture was incubated for 48 h in a $CO_2$ incubator. CV-1 cells from the culture were scraped and collected with the medium. Virus was released from the cells by 3 cycles of freezing and thawing followed by sonication for 1 min in a bath sonicator. The recombinant viral clones were selected for growth on tK-143B cells in the presence of 5-bromo-deoxyuridine (BUDr) and 5-bromo-chloro-3-indoyl-beta-D galactoside (X-gal). Blue plaques were selected and purified by at least 3 more cycles of plaque isolation. The rIL-2VV thus obtained was tested in mice for toxicity and in vitro for the absence of bacteria, fungi, and mycoplasma. The presence of vaccinia virus in the rIL-2VV preparation was confirmed by an antibody neutralization assay using anti-vaccinia polyclonal antibody. Tests were also carried out to rule out contamination with human infectious viruses such as HIV, HPV, and HBV. A seed lot was established with $10^9$ plaque forming units of rIL-2VV.

Melanoma Cell Lines

Melanoma cells were derived from five established melanoma cell lines Mel-2, Mel-3, Mel-4, Mel-6 and Mel-9. These cells were originally derived from patients with metastatic melanoma. These cells express at least two HLA class 1-A antigens. These cells also express a variety of melanoma antigens. The melanoma cell lines have been characterized for the expression of melanoma antigens that induce melanoma specific antibodies and cytolytic T cells. The cells contained characteristic melanoma cellular components such as melanosomes and pre-melanosomes that could be detected microscopically. Cells were free of contaminants such as bacteria, mycoplasma, viruses, and other biohazardous agents. A seed lot was established for each melanoma cell line. One vial from this seed lot was used for the preparation of one batch of vaccine.

Preparation of Melanoma Sonicate (MS) Containing Recombinant Vaccinia Virus (rIL-2VV-MS)

A single cell suspension of melanoma cells was exposed to rIL-2VV preparation at a ratio of about 10 cells to about 1 PFU of the rIL-2VV. The ratio can vary and can be anywhere between about 1000–0.001 cells to about 1 PFU of virus. After incubation for 24 hrs (viral replication is not yet substantially cytolytic and substantially all cells remain intact) in a $CO_2$ incubator, the melanoma cells were separated by spinning at approximately 1,200 rpm for 10 min in a refrigerated centrifuge. The supernatant (S1) was saved and the cell pellet (P1) was reconstituted in PBS. The cells were disrupted by sonication using a probe sonicator (1,500 Watts, Heat System XL series) for approximately 1 min. The sonication was repeated about three times or until all cells were broken but nuclei were still intact (as monitored under microscope). The mixture of broken cells was then spun at approximately 800 rpm for 10 min and the resulting melanoma sonicate (MS) containing vaccinia virus particles, enucleated cytosol and cell membranes was saved (the pellet containing mostly nuclei was discarded). The supernatant S1 was centrifuged at approximately 100,000 g for 30 min using an ultracentrifuge to pellet the virus from the supernatant. The pellet was combined with the nuclei-free melanoma cell sonicate (MS) to form the rIL-2VV-MS preparation. Each melanoma cell line was processed separately in the same manner. The rIL-2VV-MS from each melanoma cell line was then placed in a Petri dish about 10 cm from a germicidal UV lamp (short-wave UV, 256 nm, 1.5–1.75 microwatt/$cm^2$) for about 1 hour to inactivate the vaccinia virus. Melanoma sonicates from all five melanoma cell lines were mixed in an equal cell number ratio. One unit of rIL-2VV-MS contained the equivalent of about $10^7$ original melanoma cells and $10^6$ PFU of rIL-2VV. The rIL-2VV-MS preparations were dispensed in 1 ml vials with saline (0.9% sodium chloride solution) and stored at −70° C. until needed.

Dendritic/Monocytic Cells (DC/M)

100 ml of peripheral blood was collected from the patient and 50 ml was reserved for HLA analysis. Dendritic cells were isolated from the remaining 50 ml as follows. Peripheral blood lymphocytes (PBLs) were isolated from blood using lymphocyte separating medium (Ficoll-Hypaque or Lymphocyte Separation Medium (LSM), Litton). The blood was collected in sterile heparinized tubes, diluted in Hank's balanced salt solution (HBSS), overlaid on Ficoll-Hypaque, and centrifuged at 400 g for 30 minutes. Cells at the LSM-aqueous interface were then harvested, washed twice in HBSS, and counted in trypan blue to assess the viability. PBLs were reconstituted at $10^6$ cell/ml in RPMI-1640 complete medium with 10% FBS and 1 mM glutamine, transferred into a T75 tissue culture flask and incubated at 37° C. for 2 hrs in a $CO_2$ incubator. The flask was then washed at least 4 times with complete RPMI medium to remove non-adherent cells. After the final wash 35 ml RPMI-1640 complete medium was added to the flask followed by incubation overnight (approximately 18 hours). The next day, floating, non-adherent cells (dendritic/monocytic cells) were washed with medium and transferred to a new flask with RPMI-1640 complete medium supplemented with 2,000 unit/ml IL-4 and 2,000 unit/ml GM-CSF and incubated for 18–24 hours in a $CO_2$ incubator. (Increased DC yield can be obtained with the addition of FLT-3 ligand, which is an in vivo dendritic-cell growth factor.) The yield of DC/M was measured and the cells further cultured for about 5 days in a $CO_2$ incubator. Usually 1–5×10⁶ viable DC/M cells were obtained after 5 days of culture. (The culture period can be longer to obtain larger numbers of cells.) The day prior to the DC/M-MS administration, cultured DC/M were harvested from the flask, washed once with PBS and mixed with 1 ml unit of rIL-2VV-MS in 5 ml of AIM V (serum-free) medium containing 2,000 unit/ml IL-4 and 2,000 unit/ml GM-CSF. The passage through serum-free medium was intended to eliminate the toxic effects associated with administration to a subject of a preparation containing bovine serum. The mixture was incubated in a glass vial at 37° C. overnight (approximately 18 hours) to allow time for processing and presentation of tumor and vaccinia virus antigens. The minimal time for antigen presentation is about six hours. The next day, the resulting DC/M-MS were spun down and the supernatant was discarded (an aliquot is saved for endotoxin testing). The DC/M-MS was reconstituted in 1 ml of rIL-2VV-MS and divided into 5–6 aliquots for administration to the subject.

Monitoring the Induction of Immune Responses

Indications of induction of anti-melanoma immunity in patients treated with the melanoma vaccine are useful in determining the potency of the vaccine. These indications are especially valuable in early stages of vaccine therapy when end-point clinical results are not yet available. Induction of anti-melanoma immunity was analyzed by determining the delayed type hypersensitivity (DTH) response against melanoma antigens prior to and three months after the melanoma vaccine treatment. In addition, serum and peripheral blood lymphocytes were obtained prior to vaccine injection and one month after the vaccine injection to test the induction of anti-melanoma immunity by cytotoxicity assay, CTL precursor frequency (CTLp) assay and phenotypic analysis of lymphocytes.

Delayed Type Hypersensitivity (DTH) Test

This test was performed to evaluate the immune response against melanoma antigens. If a patient was positive to HLA A1 then melanoma peptide antigen MAGE-1 loaded-DC/M was used. If a patient was positive for HLA A2 then MAGE-3, MART-1 or gp100 melanoma antigen-loaded DC/M was used. MAGE-1 peptide has amino acid sequence $NH_2$-EADPTGHSY—COOH (SEQ ID NO: 1), MAGE-3 peptide has amino acid sequence $NH_2$-EVDPIGHLY—COOH (SEQ ID NO: 2), and MART-1 peptide has amino acid sequence $NH_2$-AAGIGILTV—COOH (SEQ ID NO: 3). The peptides were obtained from a commercial source. The purity of this peptide was >90% and showed a single peak in the mass spectrum analysis. These peptides were reconstituted in pure water at 1 mg/ml and sterilized by filtration through a 0.2 µm sterile filter. Reconstituted peptides were aliquoted at 1 ml per vial and frozen at −70° C. Ten million DC/M in 1 ml of medium containing 50–200 µg of peptide were incubated at 37° C. for 4 hours. The peptide loaded DC/M were washed two times with medium and then kept in 100 µl of PBS for injection to assess DTH response, in vitro cytotoxicity assay, proliferation, and ELISPOT assay.

For DTH test, the melanoma peptide antigen-pulsed autologous DC/M (10⁵⁻⁶) were injected subcutaneously at the deltoid region. After 48 hours, induration was measured and photographed. The patient also received plain DC/M as a control in the other arm. If a DTH site showed a response, the site was biopsied and analyzed for the presence of CTLp by CTLp frequency assay and for the presence of cytotoxic lymphocytes by the ⁵¹Cr release assay. In addition, immunohistology was performed to analyze the phenotype of tumor-infiltrating lymphocytes. DTH test was performed prior to the initiation of CVACII therapy and one month after initiation of the therapy.

Lymphocytes from Blood (PBL) and Lymphocytes from DTH Sites

Cellular assays such as CTL assay, and CTLp assay were performed using patient's peripheral blood lymphocytes (PBL) as effector cells. PBL were harvested from blood as described above. Infiltrating lymphocytes at the DTH sites were isolated from biopsies taken at the peptide pulsed DC/M-injected sites. Biopsies were also taken at the control DC/M-injected sites. Isolation of lymphocytes from the biopsy tissue was performed by collagenase treatment. Tissue was minced and kept in 10 ml of RPMI medium containing collagenase-DNase (1.4 mg of collagenase type IV and 1.0 mg of DNase per ml) for 3–4 hours at 37° C. Cells were washed 3 times with medium and kept overnight in a $CO_2$ incubator. The next day, non-adhering lymphocytes were separated from adhered fibroblast cells and cultured in the presence of IL-2 containing medium and peptide-pulsed DC/M for 1–2 months. These lymphocytes were phenotyped and tested for peptide specific CTL and CTLp.

Cytolytic Assay

MAGE-1, MAGE-3, MART-1/Melan A, or gp100 peptide-specific cytolytic activity of PBL was measured using a standard chromium release assay. Freshly prepared PBL or frozen PBL from several time intervals were tested in the same assay. Melanoma cell lines positive to both HLA-A1 and •MAGE-1 (if patient is A1 positive) or to both HLA-A2 and MAGE-3, MART-1/Melan A, or gp100 (if patient is A2 positive) and autologous DC/M-pulsed with the above peptide antigens were used as stimulators in this assay. Patient's PBL stimulated with melanoma antigen were cultured in IL-2 RPMI medium for at least 3 weeks and used in this assay. Target cells in the assay routinely included two melanoma cell lines, normal skin fibroblasts pulsed with appropriate peptide, and erythroleukemia line K-562. For the assay, target cells were harvested, washed and incubated with 100 µCi sodium chromate/10⁶ cells, in 0.5 ml volume for 60 minutes at 37° C. After washing with RPMI 1640 four times, radiolabelled target cells were added at 10⁴/ml in 100 µl volume to conical-bottomed microtiter plates (Costar). Effector to target ratios (E:T) 40:1–5:1 were used in quadruplicate wells. Plates were spun at 250 g for 5 minutes and incubated at 37° C. in a humidified incubator containing 5% $CO_2$. To determine maximum release, 0.1 ml of 1% sodium dodecyl sulfate solution was added to the appropriate wells. At the end of four hours the supernatants from the wells were harvested on fiber filters and then counted for one minute on a gamma counter. Counts per minute (cpm) were used to calculate percent release (% R) according to the formula as disclosed in Example 1.

ELISPOT Assay may be Used to Quantify the CTLp Specific to a Melanoma Peptide Antigen This assay can be performed according to a published method but with slight modification (Miyahira, Y. et al., Quantification of antigen specific CD8+ T cells using an ELISPOT assay, J. Immunol. Meth. 181:45–54, 1995). Wells in a 96 well plate are coated with 10 µg/ml mouse anti-human IFN-γ in 75 µl of PBS and incubated overnight at room temperature under a laminar flow hood. The plate is washed three times with culture medium (Complete RPMI-1640). The last wash is performed with medium. PBL, in the amounts of 10⁴, 5×10⁴, 10⁵, or 5×10⁶ PBL (10⁶ for fresh PBL) in 50 μl of medium are added in each well. At least 25 replicates are kept for each dilution. Peptide pulsed DC/M at a ratio to PBL of 1:1 are added into each well and incubated 24–48 h in a $CO_2$ incubator. Wells are washed with PBS containing 0.05% Tween 20. Fifty (50) μl (5 μg/ml) of biotinylated mouse anti-interferon-gamma (with different clone) is added per well and incubated overnight at 4° C. The next day, wells are washed three times with PBS-Tween 20 and 50 μl of avidin-peroxidase is added (as per the manufacturer's instruction). The plate is incubated at 37° C. for 1 h and washed two times with PBS-Tween and one time with PBS (no Tween-PBS). Fifty (50) μl of Tris-HCl (50 mM and pH 7.5) containing 3,3' diaminobenzidine-tetra-hydrochloride dehydrate (DAM) (1 mg/ml) and 5 μl/ml of 30% hydrogen peroxide is added and allowed to develop color. Black green spots in each well are counted using a simple microscope. The number of spots for each dilution is calculated and compared.

Immunophenotyping

Peripheral blood lymphocytes and DTH-infiltrating lymphocytes were phenotyped for CD4, CD8, CD16 and CD25 using direct or indirect immunofluorescence or immunohistologic methods. Appropriate monoclonal antibodies to CD4, CD8, CD16 and CD25 were purchased from commercial sources. DC/M were phenotyped for the expression of CD80, CD85, CD11b and Ia antigens.

Expression of IL-2 at the Vaccine Injection Site

Punch biopsies were taken from the vaccine-injected and control vaccine-injected sites. At least one vaccine biopsy and one control vaccine biopsy was taken at each time point in the injection schedule and tested for the presence of IL-2. For immunohistology, frozen biopsy tissue was used for preparation of 6 μm tissue sections on treated glass slides which were then air dried for 30 min at room temperature. Tissue was fixed with Situfix (Kreatech Diagnostics) and then washed twice with phosphate-buffered saline (PBS). A drop of appropriately diluted biotinylated antibody to human IL-2 (5 μg/ml concentration) was added and incubated in a humid chamber at room temperature for 30 minutes to 1 hour. The slide was washed three times with PBS and then incubated with appropriately diluted avidin peroxidase for 30 min. The slide was washed twice with PBS and then treated with a drop of diaminobenzidine (1.3 mM DAB in PBS containing 0.02% hydrogen peroxide) for 20–30 minutes. The slide was washed with PBS and dehydrated with alcohol and Xylene, and mounted with DPX. Brown staining indicates the presence of IL-2.

Statistical Analysis

All immunological tests compared induction of immunity in the pre- and post-treatment samples. In these analyses, an ANOVA statistical method was used to identify changes due to the vaccine therapy.

Results

The patient received six biweekly subcutaneous injections of CVACII over three months (induction phase). Clinically, no major side-effects were observed except for mild fever, headache, and inflammation and swelling at the vaccine sites. Post-vaccination, peripheral mononuclear cells contained an increased number of tumor-reactive proliferative and cytolytic cells. In general, the patient had no DTH response prior to the melanoma vaccine therapy. However, DTH response was apparent when tested after the completion of the induction phase.

Competence of immunity to common recall antigens was tested using the Multitest CMI (Pasteur-Merieux Connaught Laboratories, Swiftwater, Pa.) prior to vaccine treatment and two months after the initiation of vaccine treatment. The patient showed a reaction to at least one of the eight antigens in the Multitest prior to the treatment and exhibited a reaction to at least one of the eight recall antigens. Furthermore, the patient exhibited a vitiligo (discoloration of the skin) near the vaccine-injected sites, suggesting the induction of anti-melanocyte immune response.

Figure 6:
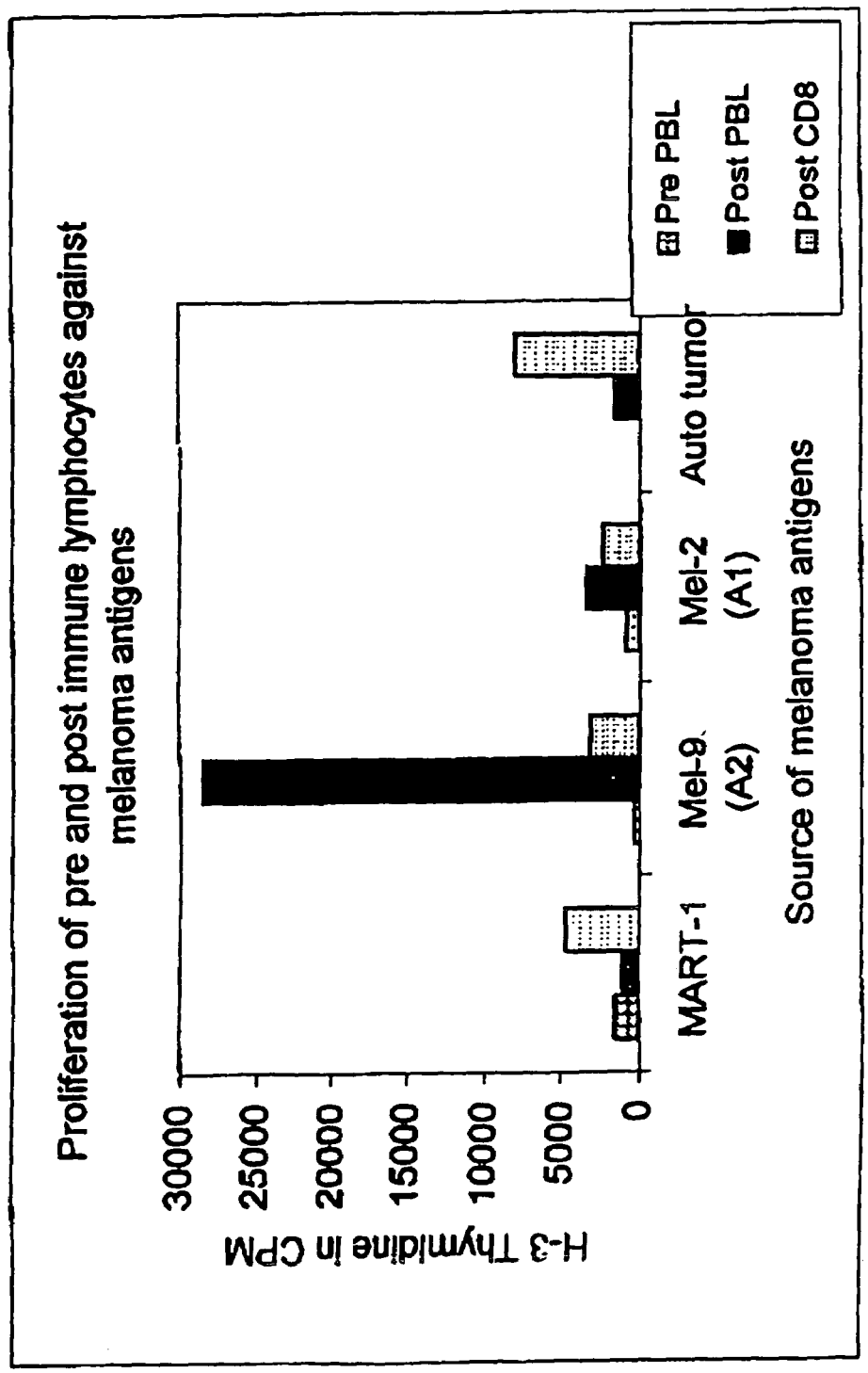
FIG. 6 shows HLA restricted proliferation of PBL and CD8 cells from a representative patient when exposed to various melanoma antigens (MART-1, Mel-9, Mel-2, and own tumor cells) as tested before and after vaccination.
Figure 7:
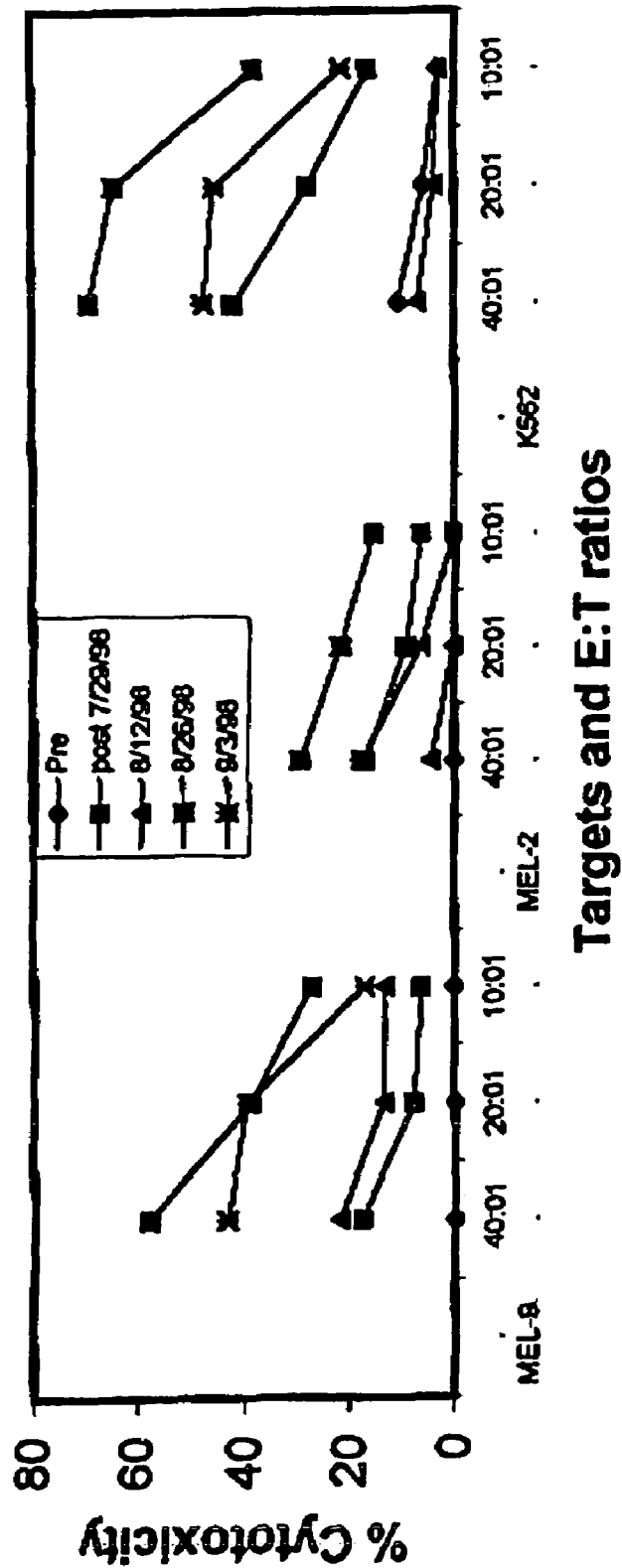
FIG. 7 shows HLA restricted cytotoxicity profile of a patient as tested at pre- and post-vaccination (at biweekly intervals) time periods.

Several in vitro assays were also performed using pre- and post-vaccination blood. Post-immune PBL showed an enhanced proliferation to melanoma antigens and increased anti-melanoma cytotoxicity (FIGS. 6 and 7 respectively). FIG. 6 shows proliferation of pre-immune PBL and post-immune PBL or fractionated $CD8^+$ T cells against autologous dendritic/monocytic cells pulsed with purified melanoma peptide antigen (MART-1), the patient's HLA-matched allogeneic melanoma cell lysate (Mel-9), melanoma cell lysate derived from melanoma cells that are not matched to the patient's HLA (Mel-2), or cell lysates from patient's own tumor cells. When compared with pre-immune PBL, post-immune PBL or $CD8^+$ T-cells showed enhanced proliferative response to all sources of melanoma antigens. FIG. 7 shows cytotoxicity of pre- and post-immune PBL of a patient immunized with the CVACII. PBL were isolated from the blood and stimulated with melanoma antigen-pulsed DC/M for 1–3 weeks in RPMI complete medium containing 10 units/ml of IL-2. When compared with pre-immune PBL, post-immune PBL showed a higher lysis against the patient's HLA-matched melanoma cells (Mel-9). Although the post-immune PBL showed an increased lysis of melanoma cells that are not sharing the patient's HLA (Mel-2), this increase was only moderate. Post-immune PBL also showed an enhanced cytotoxicity against the NK target K562. The immune reaction was specific since the patient's response was more pronounced when HLA type was matched. Several other assays such as ELISA to demonstrate the production of antibodies to melanoma antigens, immunophenotype of cells that infiltrated the DTH site and testing of the vaccine injected sites for IL-2 production were also performed. In addition, the induction of anti-melanoma immunity revealed an immune reaction against synthetic melanoma peptide antigens and the patient's own tumor cell antigen-pulsed dendritic cells. Taken together these results indicated that CVACII vaccination induced positive immunological changes this advanced, terminally-ill patient. These results demonstrate that immunization with CVACII confers cellular immunity and retards tumor growth, thus prolonging the survival of patients afflicted with melanoma.

The cited references are incorporated by reference herein in their entirety. The present invention is not to be limited in scope by the exemplified embodiments, which are intended as illustrations of single aspects of the invention. Various modifications of the invention in addition to those shown and described herein will become apparent to those skilled in the art from foregoing description and accompanying drawings. Such modifications are intended to fall within the scope of the appended claims.

What is claimed is:

1. A method for eliciting an anti-cancer immune response in a subject, which comprises:
   (a) administering a first recombinant vaccinia virus encoding at least one first immunostimulating molecule, wherein the first immunostimulating molecule is IL-2; and
   (b) administering a composition comprising antigen presenting cells, which are capable of inducing T cell activation, wherein the antigen presenting cells are dendritic cells and/or monocytes, and which are autologous or syngeneic, pulsed with a preparation comprising enucleated cytosol and cell membranes of cancer cells, which are derived from the subject or are the same cancer cell type as the patient-derived cancer cells, infected with a second recombinant vaccinia virus encoding at least one second immunostimulating molecule, wherein the second immunostimulating molecule is IL-2; and
(c) wherein administration of said first recombinant vaccinia virus and said composition is at or near lymph node(s); and wherein administration of said first recombinant vaccinia virus is approximately 30 minutes prior to said composition.

2. The method of claim 1, wherein $10^4$ to $10^8$ PFU of the first recombinant vaccinia virus is provided.

3. The method of claim 1, wherein $10^7$ PFU of the first recombinant vaccinia virus is provided.

4. The method of claim 1, wherein $10^5$ to $10^7$ antigen presenting cells are provided.

5. The method of claim 1, wherein $10^6$ to $5 \times 10^6$ antigen presenting cells are provided.

6. The method of claim 2, wherein the enucleated cytosol is substantially free of nuclei.

7. The method of claim 2, wherein the cell membranes comprise at least two HLA class I A antigens.

8. The method of claim 2, wherein the first recombinant vaccinia virus is a live virus.

9. The method of claim 2, wherein the second recombinant vaccinia virus is either live or inactivated.

10. The method of claim 2, wherein the antigen presenting cells are dendritic cells or monocytes.

11. The method of claim 2, wherein the antigen presenting cells are dendritic cells and monocytes.

12. The method of claim 2, wherein the antigen presenting cells are autologous cells.

13. The method of claim 2, wherein the antigen presenting cells are HLA-matched cells to the subject.

14. The method of claim 2, wherein the cancer cells are melanoma cells.

15. The method of claim 14, wherein the melanoma cells comprise one or more cells selected from the group consisting of Mel-2, Mel-3, Mel-4, Mel-6, and Mel-9.

16. The method of claim 2, wherein the cancer cells are established cancer cell lines.

17. The method of claim 2, wherein the cancer cells are from the subject.

18. A method of treating cancer in a subject, which comprises:
(a) administering a first recombinant vaccinia virus encoding at least one first immunostimulating molecule, wherein the first immunostimulating molecule is IL-2; and
(b) administering an effective amount of a composition comprising antigen presenting cells which are autologous or syngeneic, and which are capable of inducing T-cell activation, wherein the antigen presenting cells are dendritic cells and/or monocytes, pulsed with a preparation comprising enucleated cytosol and cell membranes of cancer cells, which are derived from the subject or the same type of cancer cells as patient-derived cancer cells, infected with a second recombinant vaccinia virus encoding at least one second immunostimulating molecule, wherein the second immunostimulating molecule is IL-2; and
(c) wherein administration of said first recombinant vaccinia virus and said composition is at or near lymph node(s); and wherein administration of said first recombinant vaccinia virus is approximately 30 minutes prior to said composition.

19. The method of claim 18, wherein $10^5$ to $10^7$ PFU of the first live recombinant vaccinia virus is provided.

20. The method of claim 18, wherein enucleated cytosol and cell membranes equivalent to $10^6$ to $10^7$ cancer cells are provided.

21. The method of claim 18, wherein at least one treatment is administered.

22. The method of claim 18, wherein said first recombinant vaccinia virus and said composition are injected subcutaneously in at least one site selected from the group consisting of an anterior thigh, an upper arm, or the anterior thorax.

23. The method of claim 18, wherein step c) is carried out near regional lymph nodes.

24. The method of claim 18, wherein steps (a) and (b) are carried out in substantially the same site.

25. The method of claim 18, wherein the cancer is a melanoma.

26. The method of claim 18, wherein the cancer cells are melanoma cells.

27. The method of claim 18, wherein the cancer is selected from the group consisting of fibrosarcoma, myxosarcoma, liposarcoma, chondrosarcoma, osteogenic sarcoma, chordoma, angiosarcoma, Kaposi's sarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, myeloma, lymphoma, and leukemia.

28. The method of claim 18, wherein the cancer cells are from cancers selected from the group consisting of fibrosarcoma, myxosarcoma, liposarcoma, chondrosarcoma, osteogenic sarcoma, chordoma, angiosarcoma, Kaposi's sarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, myeloma, lymphoma, and leukemia.

29. The method of claim 18, wherein the enucleated cytosol is substantially free of nuclei.

30. The method of claim 18, wherein the cell membranes comprise at least two HLA class I A antigens.

31. The method of claim 18, wherein the first recombinant vaccinia virus is either live or inactivated.

32. The method of claim 18, wherein the second recombinant vaccinia virus is either live or inactivated.

33. The method of claim 18, wherein the antigen presenting cells are dendritic cells or monocytes.

34. The method of claim 18, wherein the antigen presenting cells are dendritic cells and monocytes.

35. The method of claim 18, wherein the antigen presenting cells are autologous cells.

36. The method of claim 18, wherein the antigen presenting cells are HLA-matched to the subject.

37. The method of claim 18, wherein the cancer cells are from the subject.

38. The method of claim 18, wherein the subject is a human.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Unknown Organism
<220> FEATURE:
<223> OTHER INFORMATION: Description of Unknown Organism: MAGE-1

<400> SEQUENCE: 1

Glu Ala Asp Pro Thr Gly His Ser Tyr
  1               5

<210> SEQ ID NO 2
<211> LENGTH: 9
<212> TYPE: PRT
<213> ORGANISM: Unknown Organism
<220> FEATURE:
<223> OTHER INFORMATION: Description of Unknown Organism: MAGE-3

<400> SEQUENCE: 2

Glu Val Asp Pro Ile Gly His Leu Tyr
  1               5

<210> SEQ ID NO 3
<211> LENGTH: 9
<212> TYPE: PRT
<213> ORGANISM: Unknown Organism
<220> FEATURE:
<223> OTHER INFORMATION: Description of Unknown Organism: MART-1

<400> SEQUENCE: 3

Ala Ala Gly Ile Gly Ile Leu Thr Val
  1               5
```